US010377995B2

(12) United States Patent
Inouye et al.

(10) Patent No.: US 10,377,995 B2
(45) Date of Patent: *Aug. 13, 2019

(54) MUTATED GENES FOR THE CATALYTIC PROTEIN OF *OPLOPHORUS* LUCIFERASE AND USE THEREOF

(71) Applicant: JNC CORPORATION, Tokyo (JP)

(72) Inventors: Satoshi Inouye, Kanagawa (JP); Yuiko Miura, Kanagawa (JP); Junichi Sato, Kanagawa (JP)

(73) Assignee: JNC CORPORATION, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/834,147

(22) Filed: Dec. 7, 2017

(65) Prior Publication Data

US 2018/0119112 A1 May 3, 2018

Related U.S. Application Data

(62) Division of application No. 14/685,643, filed on Apr. 14, 2015, now Pat. No. 9,868,941.

(30) Foreign Application Priority Data

Apr. 16, 2014 (JP) .................. 2014-084499

(51) Int. Cl.
*C12N 9/02* (2006.01)
*C12Q 1/66* (2006.01)
*C12N 15/09* (2006.01)
*A61K 38/00* (2006.01)

(52) U.S. Cl.
CPC ............. *C12N 9/0069* (2013.01); *C12Q 1/66* (2013.01); *C12Y 113/12* (2013.01); *C12Y 113/12013* (2013.01)

(58) Field of Classification Search
None
See application file for complete search history.

(56) References Cited

U.S. PATENT DOCUMENTS

| | | | |
|---|---|---|---|
| 6,544,754 B2 | 4/2003 | Inouye | |
| 7,723,502 B2 | 5/2010 | Coleman et al. | |
| 8,557,970 B2 | 10/2013 | Encell et al. | |
| 8,586,526 B2 * | 11/2013 | Gregory | C12N 15/62 514/1.1 |
| 8,669,103 B2 | 3/2014 | Binkowski et al. | |
| 8,809,529 B2 | 8/2014 | Klaubert et al. | |
| 8,853,374 B2 | 10/2014 | Inouye et al. | |
| 2002/0102687 A1 | 8/2002 | Inouye | |
| 2004/0002127 A1 | 1/2004 | Inouye | |
| 2008/0076156 A1 | 3/2008 | Inouye et al. | |
| 2008/0199928 A1 | 8/2008 | Bernard et al. | |
| 2009/0305280 A1 | 12/2009 | Binkowski et al. | |
| 2010/0281552 A1 | 11/2010 | Encell et al. | |
| 2011/0081670 A1 | 4/2011 | Hawkins et al. | |
| 2011/0301073 A1 * | 12/2011 | Gregory | C12N 15/62 514/1.1 |
| 2012/0117667 A1 | 5/2012 | Klaubert et al. | |
| 2012/0174242 A1 | 7/2012 | Binkowski et al. | |
| 2014/0120548 A1 | 5/2014 | Encell et al. | |
| 2014/0223590 A1 | 8/2014 | Binkowski et al. | |

FOREIGN PATENT DOCUMENTS

| | | |
|---|---|---|
| GB | 2425535 A | 11/2006 |
| GB | 2479847 A | 10/2011 |
| JP | 2002-320482 A | 11/2002 |
| JP | 2008-000073 A | 1/2008 |
| JP | 4613441 B2 | 1/2011 |
| JP | 2012-525819 A | 10/2012 |
| WO | WO-03/040100 A1 | 5/2003 |
| WO | WO-2004/042010 A2 | 5/2004 |
| WO | WO-2010/127368 A1 | 11/2010 |
| WO | WO-2011/007314 A1 | 1/2011 |
| WO | WO-2011/025980 A1 | 3/2011 |
| WO | WO-2012/061529 A1 | 5/2012 |
| WO | WO-2012/061530 A2 | 5/2012 |
| WO | WO-2012/061530 A3 | 9/2012 |
| WO | WO-2013/078362 A1 | 5/2013 |
| WO | WO-2012/061530 A8 | 6/2013 |

OTHER PUBLICATIONS

Mary P. Hall, et al., "Engineered Luciferase Reporter from a Deep Sea Shrimp Utilizing a Novel Imidazopyrazinone Substrate," ACS Chem. Biol. 7, 2012, pp. 1848-1857.

Satoshi Inouye, et al., "Secretional luciferase of the luminous shrimp *Oplophorus gracilirostris*: cDNA cloning of a novel imidazopyrazinone luciferase[1]," FEBS Letters 481, 2000, pp. 19-25.

Satoshi Inouye, et al., "The Use of *Renilla* Luciferase, *Oplophorus* Luciferase, and Apoaequorin as Bioluminescent Reporter Protein in the Presence of Coelenterazine Analogues as Substrate," Biochemical and Biophysical Research Communications 233, 1997, pp. 349-353.

Satoshi Inouye, et al., "Overexpression, purification and characterization of the catalytic component of *Oplophorus* luciferase in the deep-sea shrimp, *Oplophorus gracilirostris*," Protein Expression and Purification 56, 2007, pp. 261-268.

Satoshi Inouye, et al., "C6-Deoxy coelenterazine analogues as an efficient substrate for glow luminescence reaction of nanoKAZ: The mutated catalytic 19 kDa Component of *Oplophorus* luciferase," Biochemical and Biophysical Research Communications 437, 2013, pp. 23-28.

(Continued)

*Primary Examiner* — Paul J Holland
*Assistant Examiner* — Samuel W Liu
(74) *Attorney, Agent, or Firm* — Drinker Biddle & Reath LLP

(57) ABSTRACT

A novel luciferase that is distinct from conventional luciferase has been desired. A luciferase mutant comprising an amino acid sequence in which glutamic acid at position 4, arginine at position 11, leucine at position 18 and valine at position 27 are substituted with other amino acids, in the amino acid sequence of SEQ ID NO: 2.

7 Claims, 2 Drawing Sheets

Specification includes a Sequence Listing.

(56) References Cited

OTHER PUBLICATIONS

Satoshi Inouye, et al., "Luminescence enhancement of the catalytic 19 kDa protein (KAZ) of *Oplophorus* luciferase by three amino acid substitutions," Biochemical and Biophysical Research Communications 445, 2014, pp. 157-162.
Osamu Shimomura, et al., "Properties and Reaction Mechanism of the Bioluminescence System of the Deep-Sea Shrimp *Oplophorus gracilorostris*," Biochemistry vol. 17, No. 6, 1978, pp. 994-998.
GB Application No. 1506174.0—Office Action dated Jan. 28, 2016.
Notification of Reasons for Refusal dated Sep. 12, 2017 in Japanese Patent Application No. 2014-084499 (5 pages) with an English translation (4 pages).
Hideshi Nakamura, et al., "Efficient Bioluminescence of Bisdeoxycoelenterazine with the Luciferase of a Deep-Sea Shrimp *Oplophorus*," Tetrahedron Letters, vol. 38, No. 36, 1997, pp. 6405-6406.
Satoshi Inouye, et al., "Expression, purification and luminescence properties of coelenterazine-utilizing luciferases from *Renilla, Oplophorus* and *Gaussia*: Comparison of substrate specificity for C2-modified coelenterazines," Protein Expression & Purification 88, 2013, pp. 150-156.
Osamu Shimomura, et al., "Recombinant aequorin and recombinant semi-synthetic aequorins," Biochem. J., 1990, vol. 270, pp. 309-312.
Osamu Shimomura, et al., "Semi-sysnthetic aequorin, An improved tool for the measurement of calcium ion concentration," Biochem. J., 1988, vol. 251, pp. 405-410.
Osamu Shimomura, et al., "Semi-synthetic aequorins with improved sensitivity to $Ca^{2+}$ ions," Biochem. J., 1989, vol. 261, pp. 913-920.
Katsunori Teranishi, "Luminescence of imidazo[1,2-a]pyrazin-3(7H)-one compounds," Bioorganic Chemistry 35, 2007, pp. 82-111.
Chun Wu, et al., "Chemi- and bioluminescence of coelenterazine analogues with a conjugated group at the C-8 position," Tetrahedron Letters 42, 2001, pp. 2997-3000.
GB Application No. 1403374.0—Search Report dated Nov. 12, 2014.
Inouye, et al., "Soluble protein expression in *E. coli* cells using IgG-binding domain of protein A as a solubilizing partner in the cold induced system", Biochem. Biophys. Res. Commun., 2008, 376, pp. 448-453.
GB Application No. 1406130.3—Search Report dated Nov. 11, 2014.
GB Application No. 1418471.7—Search Report dated Jun. 25, 2015.
GB Application No. 1422600.5—Search Report dated Sep. 15, 2015.
Inouye, et al., "Unconventional secretion of the mutated 19 kDa protein of Oplophorus luciferase (nanoKAZ) in mammalian cells", Biochemical and Biophysical Research Communications, Jul. 11, 2014, vol. 450, , No. 4, pp. 1313-1319.
Inouye, et al., "Codon optimization of genes for efficient protein expression in mammalian cells by selection of only preferred human codons", Protein Expr. Purif., 2015, 109, pp. 47-54.
Ngo, et al., "Computational Complexity, Protein Structure Prediction, and the Levinthal Paradox", The Protein Folding Problem and Tertiary Structure Prediction, 1994, Merz et al. (ed.), pp. 433 and 492-495.
Pichler, et al., "Imaging reversal of multidrug resistance in living mice with bioluminescence: MDR1 P-glycoprotein transports coelenterazine", Proc. Natl. Acad. Sci., 2004, vol. 101, No. 6, pp. 1702-1707.
JP 2013-080734—Office Action dated Jun. 28, 2016.
JP Application 2016-001665—Notice of Reasons for Refusal dated Oct. 16, 2016 (including English translation).
JP Application 2014-210409—Notice of Reasons for Refusal dated Mar. 20, 2018 (including English translation).

\* cited by examiner

MUTATED GENES FOR THE CATALYTIC PROTEIN OF *OPLOPHORUS* LUCIFERASE AND USE THEREOF

CROSS REFERENCE TO RELATED APPLICATIONS

This application is a divisional application of U.S. application Ser. No. 14/685,643 filed Apr. 14, 2015, which claims benefit of Japanese Application No. 2014-084499 filed on Apr. 16, 2014.

REFERENCE TO A SEQUENCE LISTING

The instant application contains a sequence listing which has been submitted in ASCII format via EFS-Web and is hereby incorporated by reference in its entirety. Said ASCII copy, created on Nov. 30, 2017, is named 206313_0016_01_570807_ST25.txt and is 19,596 bytes in size.

TECHNICAL FIELD

The present invention relates to mutated genes for the catalytic domain protein of *Oplophorus* luciferase, use thereof and so on.

BACKGROUND ART

*Oplophorus gracilirostris* luciferase from the deep-sea shrimp is a secretory-type luciferases and uses coelenterazine as a luminescence substrate (Patent Document 1, Non-Patent Document 1). *Oplophorus* luciferase consists of a 35 kDa protein and a 19 kDa protein with the molecular weight of a 106 kDa protein (Non-Patent Document 2). In *Oplophorus* luciferase, the 19 kDa protein is found to be a catalytic domain of the luminescence reaction (Non-Patent Document 2). By comparison of *Oplophorus* luciferase with other marine luciferases, it is known that the substrate specificity of *Oplophorus* luciferase is broad and coelenterazine analogues are used as good luminescence substrates (Non-Patent Document 3). Further, the substrate specificity of 19 kDa protein having a catalytic function is in good agreement with that of *Oplophorus* luciferase (Non-Patent Document 4).

Recently, it is reported that the mutated 19 kDa protein with the 16 amino acid mutations showed approximately 10-fold higher luminescence activity than that of native 19 kDa protein, and the mutated 19 kDa protein with different amino acid codons was named nanoKAZ or nanoLuc. This mutant with a signal peptide sequence for secretion was shown to be secreted from cells (Patent Document 2, Non-Patent Documents 5 and 6). In addition, the detailed studies on the 16 mutated amino acids were performed and the mutant (named eKAZ) with 3 amino acid mutations (V44I, A54I and Y138I) showed an efficient substrate for coelenterazine. However, eKAZ was not secreted efficiently from cells (Non-Patent Document 7).

On the other hand, nanoKAZ and nanoLuc showed that native coelenterazine is not used for an efficient substrate. In contrast, bis-coelenterazine, 6h-f-coelenterazine, etc. which show highly hydrophobic properties, are used for efficient substrates (Non-Patent Document 6). As these coelenterazines with high hydrophobicity showed high permeability in cell membrane, and caused a high background level of luminescence, and cannot allow to be imaging for a long period of time. From these reasons, it has been desired to develop a secreted luciferase mutant which can use native coelenterazine more efficiently and has luminescence ability as same as that of nanoKAZ.

RELATED ART DOCUMENTS

Patent Documents

[Patent Document 1] Japanese Patent No. 4,613,441
[Patent Document 2] Japanese National Publication (Tokuhyo) No. 2012-525819

Non-Patent Documents

[Non-Patent Document 1] O. Shimomura et al. (1978) Biochemistry 17: 994-998.
[Non-Patent Document 2] S. Inouye et al. (2000) FEBS Lett. 481: 19-25.
[Non-Patent Document 3] S. Inouye & O. Shimomura (1997) Biochem. Biophys. Res. Commun. 233: 349-353.
[Non-Patent Document 4] S. Inouye & S. Sasaki (2007) Protein Express. Purif. 56: 261-268.
[Non-Patent Document 5] M. P. Hall et al. (2012) ACS Chem Biol. 7: 1848-1857.
[Non-Patent Document 6] S. Inouye et al. (2013) Biochem. Biophys. Res. Commun. 437: 23-28.
[Non-Patent Document 7] S. Inouye et al. (2014) Biochem. Biophys. Res. Commun. 445: 157-162.

DISCLOSURE OF THE INVENTION

Problem to be Solved by the Invention

Under the foregoing circumstances, a novel luciferase that is distinct from conventional luciferase has been desired.

Means for Solving the Problem

The present inventors have made extensive investigations to solve the problem above, and examined the mutated positions of the reported 19 kDa protein mutants which catalyze the luminescence reaction. By selecting and combining mutations, the inventors have newly produced luciferase mutants having higher luminescence activity than that of the known mutated 19 kDa protein (nanoKAZ or nanoLuc) catalyzing the luminescence reaction, and new luciferase mutants using coelenterazine as a luminescence substrate are secreted extracellularly in the presence or absence of the eukaryotic secretory signal peptide sequences when the mutant is expressed in animal cultured cells. The present invention has thus been accomplished.

More specifically, the present invention provides the following luciferase mutants, polynucleotides, recombinant vectors, transformants, a method of producing luciferase mutants, kits, a method for performing a luminescence reaction, and so on.

[1] A luciferase mutant of (a) or (b) below:
(a) a luciferase mutant comprising an amino acid sequence in which glutamic acid at position 4, arginine at position 11, leucine at position 18 and valine at position 27 are substituted with other amino acids, in the amino acid sequence of SEQ ID NO: 2; or,
(b) a luciferase mutant comprising an amino acid sequence in which glutamic acid at position 4, arginine at position 11, leucine at position 18 and valine at position 27 are substituted with other amino acids and one or more amino acid(s) is/are substituted with other amino acid(s) at position(s) other than at positions 4, 11, 18, 27, 33, 43, 44, 54, 68, 72, 75, 90, 115, 124, 138 and 166, in the amino acid sequence of SEQ ID NO: 2, and having a luciferase activity.

[2] The luciferase mutant according to [1] above, wherein the luciferase mutant defined in (b) above is a mutant defined in (c) below:
(c) a luciferase mutant comprising an amino acid sequence in which glutamic acid at position 4, arginine at position 11, leucine at position 18 and valine at position 27 are substituted with other amino acids and 1 to 16 amino acid(s) is/are substituted with other amino acid(s) at position(s) other than at positions 4, 11, 18, 27, 33, 43, 44, 54, 68, 72, 75, 90, 115, 124, 138 and 166, in the amino acid sequence of SEQ ID NO: 2, and having a luciferase activity.

[3] The luciferase mutant according to [1] or [2] above, wherein glutamic acid at the amino acid position 4 is substituted with alanine, arginine at the amino acid position 11 is substituted with glutamine, leucine at the amino acid position 18 is substituted with glutamine, and valine at the amino acid position 27 is substituted with leucine.

[4] The luciferase mutant according to [1] above, wherein the luciferase mutant defined in (a) or (b) above is a luciferase mutant defined in (d) or (e) below:
(d) a luciferase mutant comprising an amino acid sequence of SEQ ID NO: 4;
(e) a luciferase mutant comprising an amino acid sequence in which one or more amino acid(s) is/are substituted with other amino acid(s) at position(s) other than at positions 4, 11, 18, 27, 33, 43, 44, 54, 68, 72, 75, 90, 115, 124, 138 and 166, in the amino acid sequence of SEQ ID NO: 4, and having a luciferase activity.

[5] The luciferase mutant according to [4] above, wherein the luciferase mutant defined in (e) above is a luciferase mutant defined in (f) below:
(f) a luciferase mutant comprising an amino acid sequence in which 1 to 16 amino acid(s) is/are substituted with other amino acid(s) at position(s) other than at positions 4, 11, 18, 27, 33, 43, 44, 54, 68, 72, 75, 90, 115, 124, 138 and 166, in the amino acid sequence of SEQ ID NO: 4, and having a luciferase activity.

[6] A polynucleotide comprising a polynucleotide encoding the luciferase mutant according to any one of [1] to [5] above.

[7] A recombinant vector comprising the polynucleotide according to [6] above.

[8] A transformant transformed with the recombinant vector according to [7] above.

[9] A method for producing the luciferase mutant according to any one of [1] to [5] above, which comprises the steps of culturing the transformant of [8] above and producing the luciferase mutant according to any one of [1] to [5] above.

[10] A kit comprising at least one selected from the luciferase mutant according to any one of [1] to [5] above, the polynucleotide according to [6] above, the recombinant vector according to [7] above and the transformant according to [8] above.

[11] The kit according to [10] above, further comprising a luciferin.

[12] The kit according to [11] above, wherein the luciferin is a coelenterazine analogue.

[13] The kit according to [12] above, wherein the coelenterazine analogue is coelenterazine, h-coelenterazine or f-coelenterazine.

[14] A method for performing a luminescence reaction, which comprises contacting the luciferase mutant according to any one of [1] to [5] above with a luciferin.

[15] The method according to [14] above, wherein the luciferin is a coelenterazine analogue.

[16] The method according to [15] above, wherein the coelenterazine analogue is coelenterazine, h-coelenterazine or f-coelenterazine.

[17] A method for assaying the activity of a sequence associated with promoter regulation, which comprises using the polynucleotide according to [6] above as a reporter gene and contacting a luciferase mutant encoded by the reporter gene with a luciferin.

[18] The method according to [17] above, wherein the luciferin is a coelenterazine analogue.

[19] The method according to [18] above, wherein the coelenterazine analogue is coelenterazine, h-coelenterazine or f-coelenterazine.

Effects of the Invention

The present invention provides luciferase mutants that are distinct from the known mutants. In a preferred embodiment of the invention, the luciferase mutants newly constructed exhibit a higher activity than native 19 kDa protein and/or the reported 19 kDa protein mutants having catalytic activity of luminescence when coelenterazines analogues are used as the luminescence substrate and are secreted extracellularly in the presence or absence of eukaryotic secretory signal peptide sequences when the mutants are expressed in animal cultured cells. The present invention has thus been accomplished.

MODE FOR CARRYING OUT THE INVENTION

Figure 1:
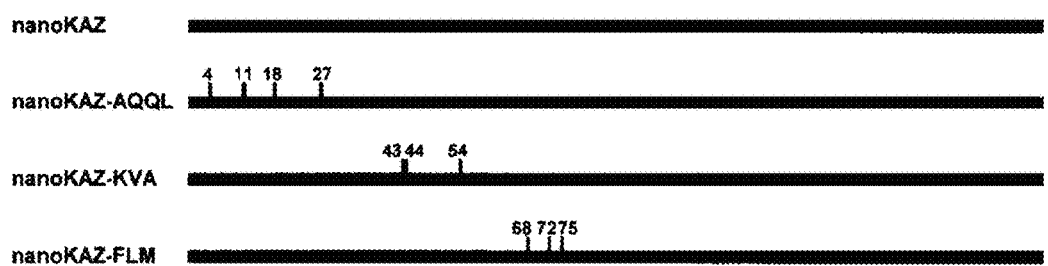
FIG. 1 is a schematic representation of nanoKAZ genes with mutations introduced at the N-terminal region, wherein the numbers designate the positions of mutated amino acids.

The present invention will be described below in detail.
1. Luciferase Mutant of the Invention The term luciferase mutant of the present invention refers to a mutant of the protein with a molecular weight of 19 kDa of *Oplophorus* luciferase. Specifically, the luciferase mutant of the present invention is intended to mean a luciferase mutant having substantially the same activity as the luciferase mutant comprising an amino acid sequence in which glutamic acid at position 4, arginine at position 11, leucine at position 18 and valine at position 27 are substituted with other amino acids in the amino acid sequence of SEQ ID NO: 2.

The term "substantially the same activity" is intended to mean at least one activity selected from luciferase activity, activity for extracellular secretion when expressed in animal cells in the presence or absence of secretory signal sequences derived from eukaryotes, and so on.

The term "luciferase activity" is intended to mean the activity for catalyzing the luminescence reaction using a luciferin (e.g., coelenterazines analogues) which serves as a substrate, namely, the reaction in which luciferin (e.g., coelenterazines analogues) is oxidized with molecular oxygen to produce oxyluciferin in its excited state. The excited state of oxyluciferin produced emits visible light and converts to the ground state of oxyluciferin.

Luminescence activity can be determined by the method described in, e.g., Inouye, S. & Shimomura, O. (1977) Biochem. Biophys. Res. Commun. 233, 349-353. Specifically, the luciferase mutant of the present invention is mixed with a luciferin to start the luminescence reaction, and the activity of catalyzing luminescence reaction can be determined using a luminometer. Commercially available luminometers, e.g., Luminescencer-PSN AB2200 (manufactured by Atto Corp.) or Centro 960 luminometer (manufactured by Berthold Inc.) may be used as luminometers.

The luciferin used in the present invention may be any luciferin as far as it serves as a substrate for the luciferase mutants of the present invention. Specifically, the luciferin used in the present invention includes a coelenterazine analogue containing the imidazopyrazinone ring as the backbone.

The coelenterazine analogue is used to mean coelenterazine or its analogues. Coelenterazine analogues include, for example, bis-coelenterazine, deoxyfuran-coelenterazine (furimazine), h-coelenterazine, hcp-coelenterazine, cp-coelenterazine, f-coelenterazine, fcp-coelenterazine, n-coelenterazine, MeO-coelenterazine, e-coelenterazine, cl-coelenterazine, ch-coelenterazine, 3iso-coelenterazine, 3meo-coelenterazine, cf3-coelenterazine, i-coelenterazine, et-coelenterazine, me-coelenterazine, 3me-coelenterazine, αmeh-coelenterazine 8-(1-naphthyl)-coelenterazine, 8-(2-naphthyl)-coelenterazine, 8-(2-thienyl)-coelenterazine, 6,8-di(2-thienyl)-coelenterazine, 8-(4-hydroxyphenyl)-coelenterazine, 8-(2-benzothienyl)-coelenterazine, 8-(b-styryl)-coelenterazine, 8-phenyl-coelenterazine, 6-deoxy-coelenterazine, 8-(3-thienyl)-coelenterazine and 8-(3-benzo[b]thienyl)-coelenterazine. Of these coelenterazines analogues, coelenterazine, h-coelenterazine or f-coelenterazine is particularly preferred in the present invention.

These coelenterazine analogues could be synthesized by publicly known methods or may also be commercially available.

The coelenterazine analogues could be synthesized by the methods described in, e.g., Shimomura et al. (1988) Biochem. J. 251, 405-410, Shimomura et al. (1989) Biochem. J. 261, 913-920, Shimomura et al. (1990) Biochem. J. 270, 309-312, Tetrahedron Lett. 38: 6405-6406, WO 2010/090319, Inouye et al. (2010) Anal. Biochem. 407, 247-252 or Inouye et al. (2013) Biocchem. Biophys. Res. Commun. 437, 23-28, or respective modifications thereof. Furimazine may be produced by the method described in Hall et al. (2012) ACS Chem. Biol. 16; 848-1857.

The coelenterazines analogues which are commercially available include, for example, coelenterazine, cf3-coelenterazine and h-coelenterazine manufactured by JNC Corp.; hcp-coelenterazine, cp-coelenterazine, f-coelenterazine, fcp-coelenterazine and n-coelenterazine manufactured by Biotium Inc.; and bis-coelenterazine manufactured by Prolume Ltd. and coelenterazine, furimazine and h-coelenterazine manufactured by Promega Corp.

The "luminescence activity using a luciferin as a substrate" refers to luminescence activity using preferably coelenterazines analogues as a substrate. Preferably, the "luminescence activity using coelenterazines analogues as a substrate" is the luminescence activity using which coelenterazine, h-coelenterazine or f-coelenterazine as the substrate.

The term "activity for extracellular secretion (secreting extracellularly) when expressed in animal cells in the presence or absence of secretory signal peptide sequences" is intended to mean that when the protein is expressed in animal cells, the expressed protein is secreted extracellularly from the endoplasmic reticulum but not via the trans-Golgi network, despite having no secretory signal peptide. The term "extracellular secretion (secreting extracellularly)" refers specifically to extracellular secretion of the protein in an amount (by weight) of 5% or more, 10% or more, or 20% or more of the expressed protein. Specific examples of the "animal cells" are those later described.

The "luciferase mutant having substantially the same activity as the luciferase mutant comprising an amino acid sequence in which glutamic acid at position 4, arginine at position 11, leucine at position 18 and valine at position 27 are substituted with other amino acids in the amino acid sequence of SEQ ID NO: 2" includes, for example, a luciferase mutant of (a) or (b) described below.

(a) A luciferase mutant comprising an amino acid sequence in which glutamic acid at position 4, arginine at position 11, leucine at position 18 and valine at position 27 are substituted with other amino acids, in the amino acid sequence of SEQ ID NO: 2; or, (b) A luciferase mutant comprising an amino acid sequence in which glutamic acid at position 4, arginine at position 11, leucine at position 18 and valine at position 27 are substituted with other amino acids and one or more amino acid(s) is/are substituted with other amino acid(s) at position(s) other than at positions 4, 11, 18, 27, 33, 43, 44, 54, 68, 72, 75, 90, 115, 124, 138 and 166, in the amino acid sequence of SEQ ID NO: 2, and having a luciferase activity.

In (a) and (b) described above, the term "glutamic acid at position 4, arginine at position 11, leucine at position 18 and valine at position 27 are substituted with other amino acids in the amino acid sequence of SEQ ID NO: 2" is intended to mean that the amino acid residues selected from the positions of 4, 11, 18 and 26 are substituted in the amino acid sequence of SEQ ID NO: 2.

The term other amino acids substituted for glutamic acid at position 4 in the amino acid sequence of SEQ ID NO: 2 includes, for example, alanine, valine, leucine, isoleucine, methionine, proline, phenylalanine, tryptophan and tyrosine, and preferably, alanine.

The term other amino acids substituted for arginine at position 11 in the amino acid sequence of SEQ ID NO: 2 includes, for example, asparagine, glutamine, serine, threonine, cysteine, lysine, histidine, aspartic acid and glutamic acid, and preferably, glutamine.

The term other amino acids substituted for leucine at position 18 in the amino acid sequence of SEQ ID NO: 2 includes, for example, asparagine, glutamine, serine, threonine, cysteine, lysine, arginine, histidine, aspartic acid and glutamic acid, and preferably, glutamine.

The term other amino acids substituted for valine at position 27 in the amino acid sequence of SEQ ID NO: 2 includes, for example, alanine, valine, leucine, isoleucine, methionine, proline, phenylalanine, tryptophan and tyrosine, and preferably, leucine.

Where glutamic acid at position 4, arginine at position 11, leucine at position 18 and valine at position 27 are substituted with other amino acids in the amino acid sequence of SEQ ID NO: 2, substitutions with alanine at position 4, with glutamine at position 11, with glutamine at position 18 and with leucine at position 27 are most preferred.

In (b) above, the term "one or more amino acid(s) is/are substituted with other amino acid(s)" is intended to mean that substitution(s) of one or a plurality of amino acid residues occur at an optional position(s) in the same sequence and at one or a plurality of positions in the amino acid sequence.

The range of "one or more" in the "one or more amino acids are substituted with other amino acids" is, for example, 1 to 35, 1 to 34, 1 to 33, 1 to 32, 1 to 31, 1 to 30, 1 to 29, 1 to 28, 1 to 27, 1 to 26, 1 to 25, 1 to 24, 1 to 23, 1 to 22, 1 to 21, 1 to 20, 1 to 19, 1 to 18, 1 to 17, 1 to 16, 1 to 15, 1 to 14, 1 to 13, 1 to 12, 1 to 11, 1 to 10, 1 to 9, 1 to 8, 1 to 7, 1 to 6, 1 to 5, 1 to 4, 1 to 3, 1 to 2 or 1. In general, the less the number of amino acids substituted, the more preferred. Such proteins may be produced by site-directed mutagenesis described in "Sambrook J. et al., Molecular Cloning: A Laboratory Manual, Third Edition, Cold Spring Harbor Laboratory Press (2001)," "Ausbel F. M. et al., Current Protocols in Molecular Biology, Supplement 1-38, John Wiley and Sons (1987-1997)," "Nuc. Acids. Res., 10, 6487 (1982)," "Proc. Natl. Acad. Sci. USA, 79, 6409 (1982)," "Gene, 34, 315 (1985)," "Nuc. Acids. Res., 13, 4431 (1985)," "Proc. Natl. Acad. Sci. USA, 82, 488 (1985)," etc.

The position(s) of the amino acids which are substituted at the positions other than at positions 4, 11, 18, 27, 33, 43, 44, 54, 68, 72, 75, 90, 115, 124, 138 and 166 in the amino acid sequence of SEQ ID NO: 2 are not particularly limited, and include position(s) 1 to 20, preferably, 1 to 16, more preferably, 1 to 14, much more preferably, 1 to 12, and most preferably, 1 to 9, selected from the group consisting of positions 1, 2, 3, 13, 14, 15, 25, 30, 36, 70, 83, 106, 128, 153, 156, 157, 159, 162, 163 and 169. In particular, the substitution positions can be position(s) 1 to 9, preferably, 1 to 8, more preferably, 1 to 7, much more preferably, 1 to 6, and most preferably, 1 to 5 (5 or less), selected from the group consisting of positions 1, 2, 3, 13, 14, 153, 159, 163 and 169.

Examples of amino acid residues which are mutually substitutable are given below. Amino acid residues in the same group are mutually substitutable.

Group A: leucine, isoleucine, norleucine, valine, norvaline, alanine, 2-aminobutanoic acid, methionine, o-methylserine, t-butylglycine, t-butylalanine and cyclohexylalanine;

Group B: aspartic acid, glutamic acid, isoaspartic acid, isoglutamic acid, 2-aminoadipic acid and 2-aminosuberic acid;

Group C: asparagine, glutamine, serine, threonine, cysteine, lysine, arginine, histidine, aspartic acid and glutamic acid;

Group D: lysine, arginine, ornithine, 2,4-diaminobutanoic acid and 2,3-diaminopropionic acid;

Group E: proline, 3-hydroxyproline and 4-hydroxyproline;

Group F: serine, threonine and homoserine; and,

Group G: phenylalanine and tyrosine.

In a preferred embodiment of the invention, the luciferase mutant is a luciferase mutant comprising the amino acid sequence of SEQ ID NO: 4.

The luciferase mutant of the present invention may further contain an additional peptide sequence at the N terminus and/or C terminus, preferably at the N terminus. The additional peptide sequence is at least one peptide sequence selected from the group consisting of a peptide sequence for purification, a peptide sequence for expressing the luciferase mutant of the present invention as a soluble protein and an epitope sequence capable of recognizing an antibody. The additional peptide sequence is preferably a peptide sequence for purification. In another preferred embodiment of the invention, the additional peptide sequence is at least one sequence selected from the group consisting of a peptide sequence for purification and a peptide sequence for expressing the luciferase mutant of the present invention as a soluble protein.

Peptide sequences employed in the art may be used as the peptide sequence for purification. The peptide sequence for purification includes, for example, a histidine tag sequence with a consecutive amino acid sequence of at least 4 histidine residues and preferably at least 6 residues, an amino acid sequence with a binding domain of glutathione S-transferase into glutathione, the amino acid sequence of Protein A, etc.

The peptide used to express the luciferase mutant of the present invention as a soluble protein includes, for example, polypeptides represented by formula $(Z)_n$. The amino acid sequences for the polypeptides represented by formula $(Z)_n$ and the nucleic acid sequences encoding the same are described in, e.g., JPA KOKAI No. 2008-99669.

Peptide sequences used in the art can be used as the epitope sequence capable of recognizing an antibody.

In some embodiments of the present invention, the additional peptide sequence in the luciferase mutant does not carry any signal peptide sequence for secretion. The "secretory signal peptide sequence" includes a secretory peptide sequence of *Gaussia* luciferase, or the like.

The method for acquiring the luciferase mutant of the invention is not particularly limited. The luciferase mutant of the invention may be a protein synthesized by chemical synthesis, or a recombinant protein produced by a genetic engineering technique. When the luciferase mutant of the invention is to be chemically synthesized, synthesis may be carried out by, for example, the Fmoc (fluorenylmethyloxycarbonyl) method or the tBoc (t-butyloxycarbonyl) method. In addition, peptide synthesizers available from Advanced ChemTech, PerkinElmer, Pharmacia, Protein Technology Instrument, Synthecell-Vega, PerSeptive, Shimadzu Corporation, etc. may also be used for chemical synthesis. When the luciferase mutant of the invention is to be produced by a genetic engineering technique, the mutant may be produced by a conventional genetic recombination technique. More specifically, the luciferase mutant of the invention may be produced by inserting a polynucleotide (e.g., DNA) encoding the luciferase mutant of the invention into a suitable expression system. The polynucleotide encoding the luciferase mutant of the invention, expression of the luciferase mutant of the invention in an expression system or the like will be later described.

2. Polynucleotide of the Invention

The present invention also provides a polynucleotide comprising a polynucleotide encoding the luciferase mutant of the invention described above. The polynucleotide of the invention may be any polynucleotide so long as it has a nucleotide sequence encoding the luciferase mutant of the invention, and a DNA is preferred. Examples of the DNA include genomic DNA, genomic DNA library, cellular or tissue cDNA, cellular or tissue cDNA library, synthetic DNA, etc. Vectors used in the libraries are not particularly limited and may be any of bacteriophages, plasmids, cosmids, phagemids, etc. Also, these vectors may be amplified directly by a Reverse Transcription Polymerase Chain Reaction (hereinafter abbreviated as RT-PCR) using the total RNA or mRNA fraction prepared from the cell or tissue described above.

The polynucleotide of the invention includes the following polynucleotides.

(i) A polynucleotide comprising a polynucleotide encoding a luciferase mutant comprising an amino acid sequence in which glutamic acid at position 4, arginine at position 11, leucine at position 18 and valine at position 27 are substituted with other amino acids, in the amino acid sequence of SEQ ID NO: 2; or, (ii) A polynucleotide comprising a polynucleotide encoding a luciferase mutant comprising an amino acid sequence in which glutamic acid at position 4, arginine at position 11, leucine at position 18 and valine at position 27 are substituted with other amino acids and one or more amino acid(s) is/are substituted with other amino acid(s) at position(s) other than at positions 4, 11, 18, 27, 33, 43, 44, 54, 68, 72, 75, 90, 115, 124, 138 and 166, in the amino acid sequence of SEQ ID NO: 2, and having a luciferase activity.

The luciferase mutants of (i) and (ii) above are as those described above.

A polynucleotide encoding a protein having a given amino acid sequence, in which one or more amino acids are substituted in the amino acid sequence, can be obtained by using a site-specific mutagenesis technique (see, e.g., Gotoh, T. et al., Gene 152, 271-275 (1995), Zoller, M. J., and Smith, M., Methods Enzymol. 100, 468-500 (1983), Kramer, W. et al., Nucleic Acids Res. 12, 9441-9456 (1984), Kramer W, and Fritz H. J., Methods. Enzymol. 154, 350-367 (1987), Kunkel, T. A., Proc. Natl. Acad. Sci. USA. 82, 488-492 (1985), Kunkel, Methods Enzymol. 85, 2763-2766 (1988); etc.), the methods using amber mutation (see, e.g., the gapped duplex method, Nucleic Acids Res., 12, 9441-9456 (1984), etc.), etc.

Alternatively, mutations may also be introduced into the polynucleotide by PCR (cf., e.g., Ho S. N. et al., Gene, 77, 51 (1989), etc.) using a pair of primers bearing on the respective 5' ends a sequence in which the targeted mutation (deletion, addition, substitution and/or insertion) has been introduced.

Also, a polynucleotide encoding a partial fragment of protein, which is one type of the deletion mutant, can be obtained using as the primers an oligonucleotide having a sequence which matches the nucleotide sequence at the 5' end of the region encoding the partial fragment to be produced in the polynucleotide encoding the target protein and an oligonucleotide having a sequence complementary to the nucleotide sequence at the 3' end thereof, and performing PCR in which the polynucleotide encoding the target protein is used as a template.

The polynucleotide of the present invention includes preferably a polynucleotide comprising a polynucleotide encoding the luciferase mutant comprising the amino acid sequence of SEQ ID NO: 4.

The polynucleotide encoding the luciferase mutant comprising the amino acid sequence of SEQ ID NO: 4 includes a polynucleotide comprising the nucleotide sequence of SEQ ID NO: 3. In another embodiment of the invention, the polynucleotide is preferably a polynucleotide comprising the nucleotide sequence of SEQ ID NO: 3.

The polynucleotide of the present invention may further contain a polynucleotide encoding an additional peptide sequence at the 5' end and/or 3' end, preferably at the 5' end. The polynucleotide encoding the additional peptide sequence includes a polynucleotide encoding at least one peptide sequence selected from the group consisting of a peptide sequence for purification, a peptide sequence for expressing the luciferase mutant of the present invention as a soluble protein, an epitope sequence capable of recognizing an antibody, and the like.

Polynucleotides comprising nucleotide sequences encoding the peptide sequence for purification employed in the art can be used as the polynucleotide encoding the peptide sequence for purification. Examples of the peptide sequence for purification include those as described above.

The polynucleotide encoding the peptide sequence used to express the luciferase mutant of the present invention as a soluble protein includes, for example, polypeptides represented by formula $(Z)_n$. The amino acid sequences for the polypeptides represented by formula $(Z)_n$ and the nucleic acid sequences encoding the same are those as described above.

Polynucleotides comprising nucleotide sequences encoding the epitope sequence capable of recognizing antibodies which are used in the art can be used as the polynucleotide encoding the antibody-recognizing epitope sequence.

In some embodiments of the present invention, the polynucleotide encoding the additional peptide sequence does not include a polynucleotide encoding a secretory signal peptide sequence. The "secretory signal peptide sequence" includes those as described above.

3. Recombinant Vector and Transformant of the Invention

The present invention further provides recombinant vectors and transformants comprising the polynucleotides of the present invention described above.

Preparation of Recombinant Vector

The recombinant vector of the invention can be obtained by ligating (inserting) the polynucleotide (DNA) of the invention to (into) an appropriate vector. More specifically, the recombinant vector can be obtained by digesting the purified polynucleotide (DNA) with a suitable restriction enzyme, then inserting into a suitable vector at the restriction enzyme site or multiple-cloning site, and ligating to the vector. The vector for inserting the polynucleotide of the invention is not particularly limited as long as it is replicable in a host, and includes plasmids, bacteriophages, animal viruses, etc. Examples of plasmids include plasmids from *E. coli* (e.g., pBR322, pBR325, pUC118, pUC119, etc.), plasmids from *Bacillus subtilis* (e.g., pUB110, pTP5, etc.) and plasmids from yeast (e.g., YEp13, YEp24, YCp50, etc.). Examples of bacteriophages include, e.g., λ phage. Examples of animal viruses include retroviruses, vaccinia viruses and insect viruses (e.g., baculoviruses). In addition, a pCold I vector, a pCold II vector, a pCold III vector and a pCold IV vector (all manufactured by Takara Bio Inc.), a pcDNA3 vector, a PICZa vector (manufactured by Invitrogen Inc.) and the like may also be suitably used.

The polynucleotide of the present invention is generally ligated in an expressible manner downstream of a promoter in a suitable vector. When the host used for transformation is an animal cell, the promoter is preferably an SV40-derived promoter, retrovirus promoter, metallothionein promoter, heat shock promoter, cytomegalovirus promoter, SRα promoter, CMV promoter, and so on. When the host is a bacterium of the genus *Escherichia*, Trp promoter, T7 promoter, lac promoter, recA promoter, λPL promoter, lpp promoter, etc. are preferred. When the host is a bacterium of the genus *Bacillus*, SPO1 promoter, SPO2 promoter, penP promoter, etc. are preferred. When the host is yeast, PHO5 promoter, PGK promoter, GAP promoter, ADH1 promoter, GAL promoter, etc. are preferred. When the host is an insect cell, polyhedrin promoter, P10 promoter, etc. are preferred.

A low-temperature expression-inducible promoter may also be suitably used. Examples of the low-temperature expression-inducible promoter include promoter sequences for cold shock genes. The cold shock gene includes, for example, *E. coli* cold shock genes (e.g., cspA, cspB, cspG, cspI and csdA), *Bacillus caldolyticus* cold shock genes (e.g., Bc-Csp), *Salmonella enterica* cold shock genes (e.g., cspE) and *Erwinia carotovora* cold shock genes (e.g., cspG). Among others, cspA promoter, cspB promoter, cspG promoter, cspI promoter, csdA promoter and the like can be advantageously used as the low-temperature expression-inducible promoter.

In addition to the foregoing, the recombinant vector of the invention may further contain, if desired, an enhancer, a splicing signal, a polyA addition signal, a ribosome binding sequence (SD sequence), a selection marker, etc., and provided for use. The selection marker includes, for example, a dihydrofolate reductase gene, an ampicillin resistance gene, a neomycin resistance gene, etc.

Preparation of Transformant

The recombinant vector thus obtained comprising the polynucleotide of the invention is introduced into an appropriate host to prepare the transformant. The host is not particularly limited as long as it is capable of expressing the polynucleotide (DNA) of the invention, and may be bacteria of the genera *Escherichia, Bacillus, Pseudomonas* and *Rhizobium*, yeast, animal cells, insect cells, etc. Bacteria of the genus *Escherichia* include *Escherichia coli*, etc. Bacteria of the genus *Bacillus* include *Bacillus subtilis*, etc. Bacteria of the genus *Pseudomonas* include *Pseudomonas putida*, etc. Bacteria of the genus *Rhizobium* include *Rhizobium meliloti*, etc. Yeast includes *Saccharomyces cerevisiae, Schizosaccharomyces pombe*, etc. Animal cells include primary cell cultures, iPS cells, cultured cell lines (CHO cells, HEK293 cells, HL-60 cells, HeLa cells, MDCK cells, NIH3T3 cells, PC12 cells), etc. Insect cells include Sf9, Sf21, etc.

The method of transfecting the recombinant vector into the host and the method of transformation by the same can be performed according to various general methods. The method for transfecting the recombinant vector into the host cell includes the calcium phosphate method (Virology, 52, 456-457 (1973)), the lipofection method (Proc. Natl. Acad. Sci. USA, 84, 7413 (1987)), the electroporation method (EMBO J., 1, 841-845 (1982)), etc. The method for transformation of the bacteria of the genus *Escherichia* includes the methods described in, e.g., Proc. Natl. Acad. Sci. USA, 69, 2110 (1972), Gene, 17, 107 (1982), etc. The method for transformation of the bacteria of the genus *Bacillus* includes the method described in Molecular & General Genetics, 168, 111 (1979), etc. The method for transforming yeast includes the method described in Proc. Natl. Acad. Sci. USA, 75, 1929 (1978), etc. The method for transformation of animal cells includes the method described in Virology, 52, 456 (1973), etc. The method for transformation of insect cells includes the method described in Bio/Technology, 6, 47-55 (1988), etc. Thus, the transformant transformed with the recombinant vector comprising the polynucleotide encoding the luciferase mutant of the invention (the polynucleotide of the invention) can be obtained.

Expression Vector and Transformant Comprising Low-Temperature Expression-Inducible Promoter Sequence An expression vector comprising the low-temperature expression-inducible promoter sequence is preferred as the expression vector among others.

Specifically, the expression vector comprising the low-temperature expression-inducible promoter sequence is intended to mean an expression vector comprising the following promoter sequence and coding sequence:

(1) a low-temperature expression-inducible promoter sequence; and,
(2) a coding sequence comprising the polynucleotide of the invention.

The low-temperature expression-inducible promoter sequence is intended to mean a promoter sequence which is capable of inducing expression of the protein by lowering the temperature from the culture conditions under which host cells can grow. Examples of the low-temperature expression-inducible promoter are promoters for genes encoding cold shock proteins (cold shock genes). Examples of the cold shock gene promoters include those as described above.

The temperature at which the low-temperature expression-inducible promoter used in the invention is capable of inducing expression is generally 30° C. or less, preferably 25° C. or less, more preferably 20° C. or less, and most preferably 15° C. or less. In order to induce the expression more efficiently, however, the expression induction is generally performed at 5° C. or more, preferably at 10° C. or more, and most preferably at approximately 15° C.

In preparing the expression vector of the invention comprising the low-temperature expression-inducible promoter sequence, the pCold I vector, pCold II vector, pCold III vector and pCold IV vector (all manufactured by Takara Bio Inc.) can be suitably used as the vector for insertion of the polynucleotide of the invention. The protein can be produced as a soluble protein in the cytoplasm in a host cell when expression is performed in a prokaryotic host cell using these vectors.

Prokaryotic cells are preferred as the host into which the expression vector comprising the low-temperature expression-inducible promoter sequence is introduced, more preferably, *Escherichia coli*, and particularly preferably, the BL21 and JM109 strains. Among others, the BL21 strain is most preferred.

Temperatures for incubation at which the transformant carrying the expression vector comprising the low-temperature expression-inducible promoter sequence grows are generally 25 to 40° C. and preferably 30 to 37° C. Temperatures for inducing the expression are generally 4 to 25° C., preferably 10 to 20° C., more preferably 12 to 18° C., and most preferably 15° C.

4. Production of Luciferase Mutant of the Invention

The present invention further provides a method for producing the luciferase mutant of the invention, which comprises the steps of culturing the transformant described above to produce the luciferase mutant of the invention. The luciferase mutant of the invention can be produced, for example, by culturing the transformant described above under conditions where the polynucleotide (DNA) encoding the luciferase mutant of the invention can be expressed, producing/accumulating and then separating/purifying the luciferase mutant of the invention.

Incubation of Transformant

The transformant of the invention can be incubated in a conventional manner used for incubation of a host. By the incubation, the luciferase mutant of the invention is produced by the transformant and accumulated within the transformant or in the culture medium.

The medium used for culturing the transformant using bacteria of the genus *Escherichia* or the genus *Bacillus* as a host may be any of a natural medium and a synthetic medium as far as it is a medium which contains carbon sources, nitrogen sources, inorganic salts, etc. necessary for growth of the transformant, and in which the transformant can efficiently grow. Examples of carbon sources which can be used are carbohydrates such as glucose, fructose, sucrose, starch, etc.; organic acids such as acetic acid, propionic acid, etc.; alcohols such as ethanol, propanol, and the like. Examples of nitrogen sources which can be used include ammonia, ammonium salts of inorganic or organic acids such as ammonium chloride, ammonium sulfate, ammonium acetate, ammonium phosphate, etc., and other nitrogen-containing compounds, and further include peptone, meat extracts, corn steep liquor, and the like. Examples of inorganic salts include monobasic potassium phosphate, dibasic potassium phosphate, magnesium phosphate, magnesium sulfate, sodium chloride, ferrous sulfate, manganese sulfate, copper sulfate, calcium carbonate, etc. If necessary, antibiotics such as ampicillin or tetracycline can be added to the medium during incubation. Where the transformant transformed with the expression vector using an inducible promoter as the promoter is cultured, an inducer may also be added to the medium, if necessary. For example, when the transformant transformed with an expression vector using a Lac promoter is cultured, isopropyl-β-D-thiogalactopyranoside (IPTG), etc. may be added to the medium and indoleacrylic acid (IAA), etc. may be added to the medium in culturing the transformant transformed with an expression vector using a trp promoter.

When the host is bacteria of the genus *Escherichia*, incubation is performed generally at approximately 15 to 43° C. for approximately 3 to 24 hours. If necessary, aeration and agitation may be applied. When the host is bacteria of the genus *Bacillus*, incubation is performed generally at approximately 30 to 40° C. for approximately 6 to 24 hours. If necessary, aeration and agitation may be applied.

Culture medium for incubation of the transformant when the host is yeast include Burkholder's minimal medium (Proc. Natl. Acad. Sci. USA, 77, 4505 (1980)) and an SD medium containing 0.5% (w/v) Casamino acids (Proc. Natl. Acad. Sci. USA, 81, 5330 (1984)). Preferably, the pH of the medium is adjusted to approximately 5 to 8. Incubation is performed generally at approximately 20 to 35° C. for approximately 24 to 72 hours. If necessary, aeration and agitation may be applied.

Culture medium for culturing the transformant when the host is an animal cell include MEM medium supplemented with approximately 5 to 20% (v/v) fetal calf serum (Science, 122, 501 (1952)), DMEM medium (Virology, 8, 396 (1959)), etc. Preferably, the pH of the medium is adjusted to approximately 6 to 8. Incubation is performed generally at approximately 30 to 40° C. for approximately 15 to 60 hours. If necessary, aeration and agitation may be applied.

Culture medium for culturing the transformant when the host is an insect cell include Grace's insect medium (Nature, 195, 788 (1962)) to which additives such as 10% (v/v) immobilized bovine serum are suitably added. Preferably, the pH of the medium is adjusted to approximately 6.2 to 6.4. Incubation is performed generally at approximately 27° C. for approximately 3 to 5 days. If necessary, aeration and agitation may be applied.

Temperatures for incubation at which the transformant transformed with the expression vector comprising the low-temperature expression-inducible promoter sequence and temperatures for expression induction are as described above.

Separation/Purification of Luciferase Mutant of the Invention

The luciferase mutant of the invention can be obtained by separating/purifying the luciferase mutant of the invention from the culture described above. As used herein, the culture is intended to mean any one of a culture broth, cultured cells or cultured bacteria and a cell lysate of the cultured cells or cultured bacteria. The luciferase mutant of the invention can be separated and purified in a conventional manner.

Specifically, when the luciferase mutant of the invention accumulates in the cultured bacteria or cultured cells, after completion of the incubation the bacteria or cells are disrupted in a conventional manner (e.g., ultrasonication, lysozyme, freezing and thawing, etc.,) and then a crude extract of the luciferase mutant of the invention can be obtained in a conventional manner (e.g., centrifugation, filtration, etc.). When the luciferase mutant of the invention accumulates in the periplasmic space, after completion of the incubation the extract containing the luciferase mutant of the invention can be obtained in a conventional manner (e.g., the osmotic shock method, etc.). When the luciferase mutant of the invention accumulates in the culture broth, after completion of the incubation the culture supernatant containing the luciferase mutant of the invention can be obtained by separating the bacteria or cells and the culture supernatant in a conventional manner (e.g., centrifugation, filtration, etc.).

The luciferase mutant of the invention contained in the extract or culture supernatant thus obtained can be purified by conventional methods of separation and purification. Examples of these methods for separation and purification which may be used include ammonium sulfate precipitation, gel filtration chromatography, ion-exchange chromatography, affinity chromatography, reversed phase high performance liquid chromatography, dialysis, ultrafiltration, etc., alone or in a suitable combination thereof. When the luciferase mutant of the invention contains the peptide sequence for purification described above, it is preferred to perform purification using the same. Specifically, when the luciferase mutant of the invention contains a histidine tag sequence, nickel chelate affinity chromatography may be used; when the luciferase mutant of the invention contains the binding domain of S-transferase to glutathione, affinity chromatography with a glutathione-binding gel may be used; when the luciferase mutant of the invention contains the amino acid sequence of Protein A, antibody affinity chromatography may be used.

5. Use of Luciferase Mutant of the Invention

Use as Detection Marker by Luminescence

The luciferase mutant of the invention can be used as a detection marker which emits luminescence in the presence of a luciferin (hereinafter "detection marker of the present invention"). The detection marker of the present invention can be utilized for detection of the target substance in, e.g., an immunoassay, a hybridization assay, etc.

The luciferase mutant of the invention can be expressed, e.g., as a fusion protein with a target protein, and introduced into cells by means of the microinjection method, etc., and the resulting product can be used to determine distribution of the target protein described above. The distribution of such a target protein or the like can be determined by using detection methods such as luminescence imaging. In addition to the introduction into cells by means of the microinjection method or the like, the luciferase mutant of the invention can be expressed in cells to provide for use.

The luminescence substrate (luciferin) used is preferably coelenterazines analogues, and particularly preferably, coelenterazine, h-coelenterazine or f-coelenterazine, as described above.

Use as Reporter Protein

The luciferase mutant of the invention may also be used as a reporter protein to assay the transcription activity of promoters, etc. In this case, the polynucleotide of the invention is used as a reporter gene and the luciferase mutant encoded by the reporter gene is contacted with luciferin. As used herein, the term "contact" is intended to mean that the luciferase mutant of the invention and a luciferin are allowed to be present in the same reaction system or culture system, which includes, for example, addition of a luciferin to a culture container charged with cells expressing the luciferase mutant of the invention, mixing the cells with a luciferin, and incubation of the cells in the presence of a luciferin. The polynucleotide encoding the luciferase mutant of the invention (i.e., the polynucleotide of the invention) is fused to a target promoter or some other expression control sequence (e.g., an enhancer, etc.) to construct a vector. By introducing the vector into a host cell and detecting the luminescence from the luciferase mutant of the invention in the presence of a luciferin (luminescence substrate), the activity of the target promoter or some other expression control sequence can be assayed. Furthermore, the expressed luciferase mutant is reacted with coelenterazine analogues and the luminescence generated may also be visualized in pictures by using a high-sensitive detector.

The luciferin used is preferably coelenterazine analogues, and particularly preferably, coelenterazine, h-coelenterazine or f-coelenterazine, as described above.

The cells used are preferably animal cells. In a preferred embodiment of the invention, the luciferase mutant is secreted outside of cells even in the case of animal cells.

The polynucleotide of the invention can be used as a reporter gene in such a manner as described above.

Material for Amusement Supplies

The luciferase mutant of the invention has the activity of catalyzing the reaction where a luciferin is oxidized with oxygen molecules to form oxyluciferin in its excited state. The oxyluciferin in the excited state emits visible light to decay to the ground state. Accordingly, the luciferase mutant of the invention can be used preferably as a luminescent material for amusement supplies. Examples of such amusement supplies are luminescent soap bubbles, luminescent ice bars, luminescent candies, luminescent color paints, etc. These amusement supplies of the invention can be prepared in a conventional manner.

The luciferin used is preferably coelenterazine analogues, and particularly preferably, coelenterazine, h-coelenterazine or f-coelenterazine, as described above.

Bioluminescence Resonance Energy Transfer (BRET) Method

By utilizing the principle of interaction between molecules by the bioluminescence resonance energy transfer (BRET) method, the luciferase mutant of the invention is available for analytical methods such as analysis of physiological functions, assay of enzyme activities, etc.

For instance, when the luciferase mutant of the invention is used as a donor and the fluorescent substance (e.g., an organic compound, a fluorescent protein, etc.) is used as an acceptor, the interactions between the donor and acceptor above can be detected by inducing bioluminescence resonance energy transfer (BRET) between them.

In an embodiment of the present invention, the organic compound used as an acceptor includes Hoechist3342, Indo-1, DAP1, etc. In another embodiment of the present invention, the fluorescent protein used as an acceptor includes a green fluorescent protein (GFP), a blue fluorescent protein (BFP), a muted GFP fluorescent protein, phycobilin, etc.

In a preferred embodiment of the present invention, the physiological functions to be analyzed include an orphan receptor (especially, a G protein-coupled receptor), apoptosis, transcription regulation by gene expression, etc. In a further preferred embodiment of the present invention, the enzyme to be analyzed is protease, esterase, kinase, or the like.

Analysis of the physiological functions by the BRET method can be performed by known methods, for example, by modifications of the method described in Biochem. J. 2005, 385, 625-637 or Expert Opin. Ther Tarets, 2007 11: 541-556. Enzyme activities may also be assayed by known methods, for example, by modifications of the method described in Nature Methods 2006, 3:165-174 or Biotechnol. J. 2008, 3:311-324.

The luminescence substrate (luciferin) used is preferably coelenterazines analogues, and particularly preferably, coelenterazine, h-coelenterazine or f-coelenterazine, as described above.

6. Kit of the Invention

The present invention also provides a kit comprising any one selected from the luciferase mutant of the invention, the polynucleotide of the invention, the recombinant vector of the invention and the transformant of the invention. The kit of the invention may further contain a luciferin.

The luciferin is preferably coelenterazines analogues, and particularly preferably, coelenterazine, h-coelenterazine or f-coelenterazine, as described above.

The kit of the present invention may be prepared with conventional materials by conventional methods. The kit of the present invention may further contain, e.g., sample tubes, plates, instructions for the kit user, solutions, buffers, reagents, and samples suitable for standardization or control samples. The kit of the present invention may further contain salts including halide ions.

The kit of the present invention can be used for the aforesaid measurement using a reporter protein or a reporter gene, the detection marker with luminescence, or the analysis of physiological functions or measurement of enzyme activities by the BRET method. The kit can also be used in the method for luminescence reaction as described below.

7. Method for Luminescence Reaction

Luminescence Activity

The luciferase mutant of the invention has the ability of catalyzing the reaction which involves oxidization of a luciferin with oxygen molecules to form an oxyluciferin in its excited state. The oxyluciferin in the excited state emits light on returning to the ground state. That is, the luciferase mutant of the invention catalyzes the luminescence reaction in which a luciferin serves as a substrate to cause luminescence. This activity is sometimes referred to as "the luminescence activity" in the specification.

Luminescence Reaction

The luminescence reaction using the luciferase mutant of the invention in which a luciferin is used as a substrate can be performed by contacting the luciferase mutant of the invention with the luciferin. As used herein, the term "contact" is intended to mean that the luciferase mutant of the invention and a luciferin are allowed to be present in the same reaction system, which includes, for example, addition of the luciferase mutant of the invention to a container charged with a luciferin, addition of a luciferin to a container charged with the luciferase mutant of the invention and mixing the luciferase mutant of the invention with a luciferin. The reaction can be carried out under conditions conventionally used for the luminescence reaction using *Oplophorus* luciferase or under conditions modified therefrom.

Specifically, solvents for the reaction which are employed are, for example, a buffer solution such as Tris-HCl buffer, sodium phosphate buffer, etc., water, and the like.

Temperatures for the reaction are generally approximately 4° C. to 40° C. and preferably approximately 4° C. to 25° C. In the reaction solution, pH is generally approximately 5 to 10, preferably approximately 6 to 9, more preferably approximately 7 to 8 and most preferably approximately 7.5.

The luciferin is preferably coelenterazines analogues, and particularly preferably, coelenterazine, h-coelenterazine or f-coelenterazine, as described above.

The luciferin may also be added to the reaction system in the form of a solution in a polar solvent such as dimethylformamide, dimethylsulfoxide, etc., or in an alcohol such as methanol, ethanol, butanol, etc.

Activation of Luminescence Activity

Luciferase activity of the luciferase mutant of the invention can be activated by halide ions, nonionic surfactants, etc.

Examples of the halide ions are fluorine ions, chlorine ions, bromine ions and iodine ions; preferred are chlorine ions, bromine ions and iodine ions.

The concentration of halide ions is generally approximately 10 µM to 100 mM, preferably approximately 100 µM to 50 mM and particularly preferably approximately 1 mM to 20 mM.

Addition of the halide ions to the reaction system is performed by a method which comprises adding the halide ions in a salt form. The salts used are alkali metal salts such as sodium salts, potassium salts, etc.; alkaline earth metal salts such as calcium salts, magnesium salts, barium salts, etc. More specific examples are NaF, NaCl, NaBr, NaI, KF, KCl, KBr, KI, $CaF_2$, $CaCl_2$, $CaBr_2$, $CaI_2$, $MgF_2$, $MgCl_2$, $MgBr_2$, $MgI_2$, etc.

Examples of nonionic surfactants which are commercially available (trade name) include Tween 20 (polyoxyethylene sorbitan monolaurate), Tween 80 (polyoxyethylene sorbitan monooleate), Triton X-100 (polyethylene glycol-p-isooctylphenyl ether), Briji-58 (polyoxyethylene (20) cetyl ether), Nonidet P-40 (ethylphenolpoly(ethylene glycol ether)n), etc., and preferably, Tween 20, Triton X-100, etc.

Concentration of the nonionic surfactant is generally approximately 0.0002% (w/v) to 0.2% (w/v), preferably, approximately 0.001% (w/v) to 0.1% (w/v), and particularly preferably, approximately 0.05% (w/v) to 0.02% (w/v).

Regardless of their purposes, all of the documents and publications described in the specification are incorporated herein by reference, each in its entirety.

Unless otherwise indicated with respect to the embodiments and working examples, the methods described in standard sets of protocols such as J. Sambrook, E. F. Fritsch & T. Maniatis (Ed.), Molecular cloning, a laboratory manual (4th edition), Cold Spring Harbor Press, Cold Spring Harbor, N.Y. (2012); F. M. Ausubel, R. Brent, R. E. Kingston, D. D. Moore, J. G. Seidman, J. A. Smith, K. Struhl (Ed.), Current Protocols in Molecular Biology, John Wiley & Sons Ltd., etc. or modifications or variations thereof are used. When commercially available reagent kits or measuring apparatuses are used, protocols attached thereto are used unless otherwise indicated.

The objects, characteristics and advantages of the present invention as well as the idea thereof are apparent to those skilled in the art from the descriptions given herein. Based on the description given herein, those skilled in the art can easily reproduce the present invention.

It can be understood that the embodiments of the invention, specific working examples, etc. are disclosed as preferred embodiments of the present invention. These descriptions are only for illustrative and explanatory purposes and are not intended to restrict the invention thereto. It is further apparent to those skilled in the art that various modifications may be made based on the descriptions given herein within the intent and scope of the present invention disclosed herein.

EXAMPLES

Hereinafter, the present invention will be described with reference to specific examples but is not deemed to be limited thereto.

Example 1: Preparation of NanoKAZ Gene with Mutation Introduced at the N-Terminal Region The nanoKAZ gene with mutation introduced at the N-terminal region was prepared by PCR in accordance with the procedure described in Ho et al., Gene (1989) 77: 51-59. Specifically, PCR was performed at two positions (cycle conditions: 25 cycles of 1 min/94° C., 1 min/50° C. and 1 min/72° C.) with a PCR kit (manufactured by Takara Bio Inc.) using as a temperate pcDNA3-GLsp-dnKAZ and four PCR primers. The second PCR was carried out using the two amplified DNA fragments as templates to prepare the mutant gene.

Construction of pcDNA3-GLsp-dnKAZ used as a template was performed as follows.

First, gene amplification was performed by PCR using a template of pCold-ZZ-P-nanoKAZ described in Inouye et al. (2013) Biochem. Biophys. Res. Commun. 437: 23-28 and the following primers.

nanoKAZ-1N/EcoRI (5' gcgGAATTCTTCACCCTGGAG-GACTTCGTCGGC 3': EcoRI sequence underlined) (SEQ ID NO: 9)

nanoKAZ-3C/XbaI (5' gccTCTAGATTAGGCCAGGAT-TCTCTCGCACAGTCT 3': XbaI sequence underlined) (SEQ ID NO: 10)

Next, a novel expression vector pcDNA3-GLsp in animal cultured cells was constructed. Specifically, the secretory signal peptide sequence of *Gaussia* luciferase was obtained from pcDNA3-GLuc vector (manufactured by Prolume Ltd.) by PCR using the following primers.

```
GLsp-1R/EcoRI
                                      (SEQ ID NO: 11)
(5' ggc GAA TTC GGT GGG CTT GGC CTC GGC CAC 3', EcoRI sequence underlined)

T7
                                      (SEQ ID NO: 12)
(5' TAATACG ACTCACTATAGGG 3')
```

The PCR was followed by digestion of the DNA fragment with HindIII/EcoRI and the resultant fragment was inserted into the HindIII-EcoRI site of pcDNA3 vector (manufactured by Invitrogen Inc.) to construct a novel expression vector pcDNA3-GLsp. The novel expression vector is under the control of the CMV promoter, followed by the Kozak sequence, the secretory signal peptide sequence of *Gaussia* luciferase and a multiple-cloning site sequence.

The DNA fragment obtained by PCR using pCold-ZZ-P-nanoKAZ as a template was digested with the restriction enzymes of EcoRI/XbaI in a conventional manner and then ligated to the EcoRI-XbaI site of pcDNA3-GLsp to construct the expression vector pcDNA3-GLsp-dnKAZ. The gene sequence inserted was confirmed by sequencing using a DNA Sequencer (manufactured by ABI Inc.).

For example, the nanoKAZ-AQQL gene with mutation introduced at the N-terminal region was constructed as follows. First, the DNA fragments amplified by the following primers were prepared using pcDNA3-GLsp-nanoKAZ as a template. Primers used to prepare the DNA fragment at the first position:

T7

(SEQ ID NO: 12)

(5' TAA TAC GAC TCA CTA TAG GG 3')

nKAZ-2R/AQQL (SEQ ID NO: 13)

(5' CAG GCT GCT CAA GCC GCC CTG CTC CAG GAC CTG

GTC TTG GTT GTA GCC GGC GGT CTG TTG CCA GTC GCC

GAC GAA GTC TGC CAG GGT GAA GAC 3')

Primers used to prepare the DNA fragment at the second position:

nKAZ-1F/AQQL (SEQ ID NO: 14)

(5' TTC ACC CTG GCA GAC TTC GTC GGC GAC TGG CAA

CAG ACC GCC GGC TAC AAC CAA GAC CAG GTC CTG GAG

CAG GGC GGC TTG AGC AGC CTG TTC 3')

BGH-R (SEQ ID NO: 15)

(5' TAG AAG GCA CAG TCG AGG 3')

The second PCR was carried out using the DNA fragments obtained above at the two positions and two PCR primers: T7 (SEQ ID NO: 12) and BGH-R (SEQ ID NO: 15). Thus, the nanoKAZ-AQQL gene with substitutions of glutamic acid at the amino acid position 4 to alanine, glutamine for arginine at amino acid position 11, glutamine for leucine at amino acid position 18 and leucine for valine at amino acid position 27, in the amino acid sequence of SEQ ID NO: 2 encoded by the nanoKAZ gene was prepared (the nucleotide sequence and amino acid sequence are shown by SEQ ID NO: 3 and SEQ ID NO: 4, respectively).

The nanoKAZ-KVA gene (the nucleotide sequence and amino acid sequence are shown by SEQ ID NO: 5 and SEQ ID NO: 6, respectively) and the nanoKAZ-FLM gene (the nucleotide sequence and amino acid sequence are shown by SEQ ID NO: 7 and SEQ ID NO: 8, respectively) with mutations introduced at the N-terminal region using the primers listed in TABLE 1 were constructed in a similar manner. FIG. 1 shows a schematic representation of the nanoKAZ mutants into which mutations were introduced.

TABLE 1

Templates and PCR primers used to construct the nanoKAZ-AQQL, nanoKAZ-KVA and nanoKAZ-FLM proteins

| Clone | | Template | | Primer | Sequence |
|---|---|---|---|---|---|
| pcDNA3-GLsp-nKAZ-AQQL | 1st PCR | pcDNA3-GLsp-nanoKAZ-EX | a<br>b | T7<br>nKAZ-2R/AQQL | 5' TAA TAC GAC TCA CTA TAG GG 3' (SEQ ID NO: 12)<br>5' CAG GCT GCT CAA GCC GCC CTG CTC CAG GAC CTG GTC TTG GTT GTA GCC GGC GGT CTG TTG CCA GTC GCC GAC GAA GTC TGC CAG GGT GAA GAC 3' (SEQ ID NO: 13) |
| | | pcDNA3-GLsp-nanoKAZ-EX | c<br>d | nKAZ-1F/AQQL<br>BGH-R | 5' TTC ACC CTG GCA GAC TTC GTC GGC GAC TGG CAA CAG ACC GCC GGC TAC AAC CAA GAC CAG GTC CTG GAG CAG GGC GGC TTG AGC AGC CTG TTC 3' (SEQ ID NO: 14)<br>5' TAG AAG GCA CAG TCG AGG 3' (SEQ ID NO: 15) |
| | 2nd PCR | 1st PCR product | a<br>d | T7<br>BGH-R | 5' TAA TAC GAC TCA CTA TAG GG 3' (SEQ ID NO: 12)<br>5' TAG AAG GCA CAG TCG AGG 3' (SEQ ID NO: 15) |
| pcDNA3-GLsp-nKAZ-KVA | 1st PCR | pcDNA3-GLsp-nanoKAZ-EX | a<br>b | T7<br>nKAZ-4R/KVA | 5' TAA TAC GAC TCA CTA TAG GG 3' (SEQ ID NO: 12)<br>5' GTG GAT GTC AGC CTT CAG GCC GTT CTC GCC GCT AAG GAC AAC TTT CTG GAT GGG GGT 3' (SEQ ID NO: 16) |
| | | pcDNA3-GLsp-nanoKAZ-EX | c<br>d | nKAZ-3F/KVA<br>BGH-R | 5' CCC ATC CAG AAA GTT GTC CTT AGC GGC GAG AAC GGC CTG AAG GCT GAC ATC CAC GTC 3' (SEQ ID NO: 17)<br>5' TAG AAG GCA CAG TCG AGG 3' (SEQ ID NO: 15) |
| | 2nd PCR | 1st PCR product | a<br>d | T7<br>BGH-R | 5' TAA TAC GAC TCA CTA TAG GG 3' (SEQ ID NO: 12)<br>5' TAG AAG GCA CAG TCG AGG 3' (SEQ ID NO: 15) |
| pcDNA3-GLsp-nKAZ-FLM | 1st PCR | pcDNA3-GLsp-nanoKAZ-EX | a<br>b | T7<br>nKAZ-6R/FLM | 5' TAA TAC GAC TCA CTA TAG GG 3' (SEQ ID NO: 12)<br>5' CTT GAA GAT CAT CTC GAT TAG CCC ATC TGA AAG CCG CTC AGC 3' (SEQ ID NO: 18) |
| | | pcDNA3-GLsp-nanoKAZ-EX | c<br>d | nKAZ-5F/FLM<br>BGH-R | 5' CTG AGC GGC TTT CAG ATG GGC TAA TCG AGA TGA TCT TCA AGT C 3' (SEQ ID NO: 19)<br>5' TAG AAG GCA CAG TCG AGG 3' (SEQ ID NO: 15) |
| | 2nd PCR | 1st PCR product | a<br>d | T7<br>BGH-R | 5' TAA TAC GAC TCA CTA TAG GG 3' (SEQ ID NO: 12)<br>5' TAG AAG GCA CAG TCG AGG 3' (SEQ ID NO: 15) |

Example 2: Construction of E. Coli Expression Vectors for ZZ-Fused NanoKAZ Mutants The mutants were expressed in E. coli as a ZZ-fused protein. Specifically, the expression vector pCold-ZZ-P-X (described in Inouye & Sahara, Protein Express. Purif. (2009) 66:52-57) was used to express the nanoKAZ mutant proteins as soluble proteins in E. coli.

The mutated gene fragment obtained in EXAMPLE 1 was purified using a PCR purification kit (manufactured by QIAGEN). After digestion with the restriction enzymes of EcoRI/XbaI, the fragment was ligated to the EcoRI-XbaI site of pCold-ZZ-X to construct the following expression vectors for the ZZ-fused nanoKAZ mutants: pCold-ZZ-P-nKAZ-AQQL, pCold-ZZ-P-nKAZ-KVA and pCold-ZZ-P-nKAZ-FLM. The gene sequence inserted was confirmed by sequencing using a DNA Sequencer (manufactured by ABI Inc.)

Example 3: Expression of ZZ-Fused NanoKAZ Mutants in Escherichia Coli

The recombinant plasmids prepared in EXAMPLE 2 and pCold-ZZ-P-nanoKAZ as a control vector were used to express the ZZ-fused nanoKAZ mutants in *Escherichia coli*.

The DNA fragment obtained in EXAMPLE 1 was digested with the restriction enzymes of EcoRI/XbaI in a conventional manner and then ligated to the EcoRI-XbaI site of pCold-ZZ-P-X to construct pCold-ZZ-P-nanoKAZ. The gene sequence inserted was confirmed by sequencing using a DNA Sequencer (manufactured by ABI Inc.).

Figure 2:
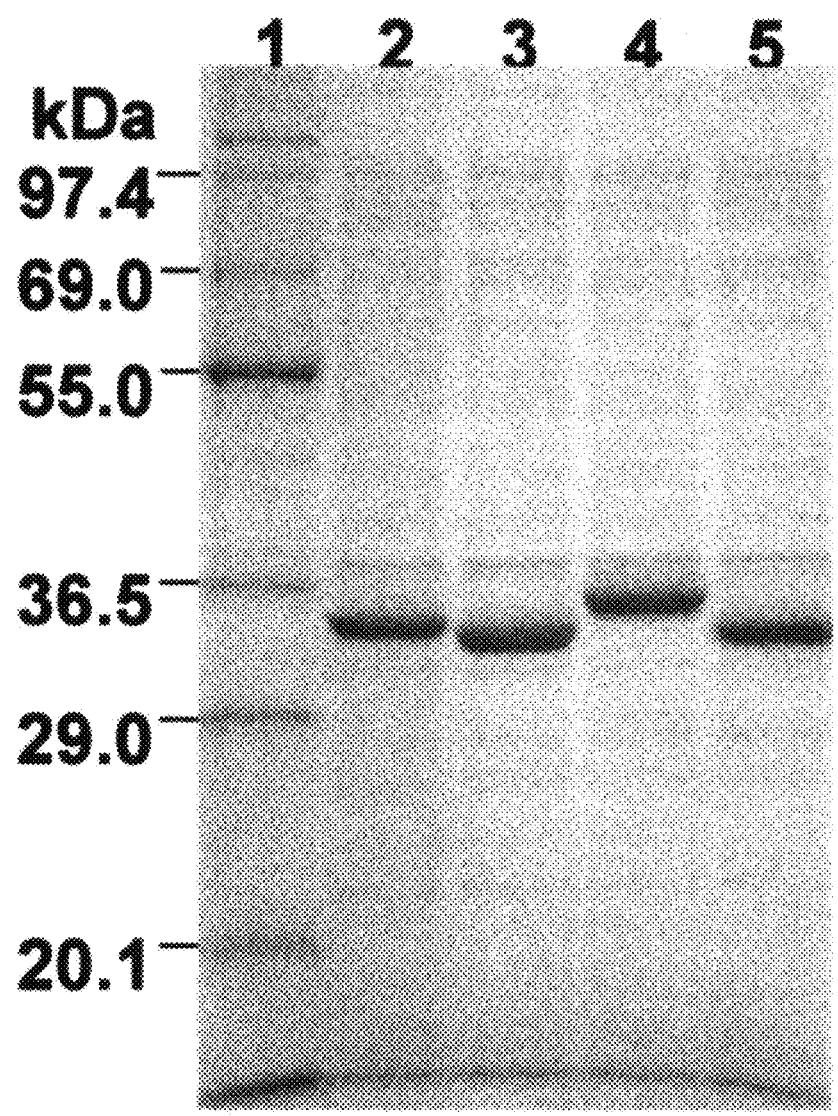
FIG. 2 shows the results of SDS-PAGE analysis of the crude enzyme solution (crude extract) of *Escherichia coli* in which nanoKAZ mutants were expressed using a pCold-ZZ-P vector.

The *E. coli* BL21 strain (manufactured by Novagen) was used as a host cell. The strain was cultured in 10 mL of Luria-Bertani medium containing ampicillin (50 µg/mL) at 37° C. for 18 hours. The seed culture was inoculated to 10 mL of LB medium and incubated for 3 hours, followed by cooling in an ice-water bath for 1 hour. IPTG was added to the culture medium at a final concentration of 0.2 mM, followed by incubation at 15° C. for further 20 hours. The *E. coli* cells were collected from 1 mL of the culture medium by centrifugation. The collected *E. coli* cells were suspended in 0.5 mL of 50 mM Tris-HCl (pH 7.6) containing 10 mM EDTA (manufactured by Wako Pure Chemical Industries, Ltd.). The cells were disrupted by sonication for 5 seconds using a Branson Model 250 Sonifire. The cells were subjected to high-speed centrifugation to recover 0.5 mL of the supernatant as a soluble fraction containing the ZZ-fused nanoKAZ mutant. This soluble fraction, 5 µL, was subjected to SDS-PAGE electrophoresis to confirm expression of the proteins. The results are shown in FIG. 2. In FIG. 2, numerals 1 to 5 represent as follows: 1: molecular weight size markers; 2: nanoKAZ, 3: nanoKAZ-AQQL, 4: nanoKAZ-KVA, 5: nanoKAZ-FLM. The results in FIG. 2 reveal that each mutated nanoKAZ protein was expressed in *E. coli* as soluble proteins at the same expression level as in nanoKAZ.

Example 4: Assay for Luminescence Activity of NanoKAZ Mutants

After 5 µL of the soluble fraction solution obtained in EXAMPLE 3 was added to 100 µL, of 50 mM Tris-HCl (pH 7.6)-10 mM EDTA containing 1 µg of coelenterazine (manufactured by JNC Corp.) or its analogue, a luminescence reaction was started. Luminescence activity was measured for 60 seconds using a luminometer (manufactured by Atto Inc.: AB2200). The relative maximum intensity of luminescence ($I_{max}$) and the integrated values for 60 seconds within parentheses in terms of relative intensity of luminescence are shown in TABLE 2.

Example 5: Substrate Specificities for ZZ-Fused NanoKAZ Mutants

The coelenterazine analogues used for substrate specificity studies were synthesized by the methods described in publications, respectively. Specifically, bis-coelenterazine was synthesized by the method described in Nakamura et al. (1997) Tetrahedron Lett. 38: 6405-6406, furimazine by the method described in Hall et al. (2012) ACS Chem. Biol. 16; 848-1857, h-coelenterazine by the method described in Inouye et al (2010) Anal. Biochem. 407:247-252 and 6h-coelenterazine and 6h-f-coelenterazine by the method described in Inouye et al (2013) Biochem. Biophys. Res. Commun. 437: 23-28. f-coelenterazine was purchased from Prolume Ltd. Luminescence activity of the ZZ-fused nanoKAZ mutants was measured by the method described in EXAMPLE 4.

The results are shown in TABLE 2. The results of TABLE 2 reveal that when coelenterazine (CTZ) was used as the luminescence substrate, the maximum luminescence intensity of nanoKAZ-AQQL was approximately 20-fold higher than that of nanoKAZ. When h-coelenterazine and f-coelenterazine were used among coelenterazine analogues, nanoKAZ-AQQL showed approximately 30-fold higher and 20-fold higher than nanoKAZ, respectively, as compared to when coelenterazine (CTZ) was used as the substrate.

TABLE 2

Luminescence substrate and substrate specificity of ZZ-fused nanoKAZ mutants expressed in E. coli

| Luminescence substrate | Relative maximum intensity of luminescence $I_{max}$ (integrated values of relative intensity of luminescence for 1 min) | | | |
| --- | --- | --- | --- | --- |
| | nanoKAZ | nanoKAZ-AQQL | nanoKAZ-KVA | nanoKAZ-FLM |
| Coelenterazine (CTZ) | 1.0 (1.0) | 19.3 (11.6) | 0.6 (0.6) | 0.3 (0.3) |
| bis-coelenterazine | 9.0 (6.3) | 4.8 (4.9) | 11.1 (7.5) | 5.7 (3.2) |
| h-coelenterazine | 14.2 (7.4) | 28.9 (10.5) | 9.1 (4.7) | 9.5 (6.5) |
| 6h-coelenterazine | 0.6 (0.4) | 5.4 (3.9) | 0.1 (0.1) | 0.2 (0.1) |
| f-coelenterazine | 20.2 (10.0) | 21.0 (8.0) | 17.4 (7.2) | 10.9 (5.9) |
| 6h-f-coelenterazine | 7.9 (4.6) | 4.6 (5.0) | 11.9 (7.7) | 9.0 (4.7) |
| Furimazine | 4.8 (3.7) | 2.3 (2.6) | 5.4 (3.6) | 3.0 (2.3) |

Example 6: Construction of Vectors for Secretory Expression of NanoKAZ Mutants in Animal Culture Cells Using Secretory Signal Peptide Sequence of *Gaussia* Luciferase Vectors for secretory expression of nanoKAZ mutants in animal culture cells were constructed as follows, using the secretory signal peptide sequence of *Gaussia* luciferase.

The mutated gene fragment prepared in EXAMPLE 1 was purified using a PCR purification kit (manufactured by QIAGEN). After digestion with the restriction enzymes of EcoRI/XbaI in a conventional manner, the fragment was ligated to the EcoRI-XbaI site of pcDNA3-GLsp vector to construct the expression vectors of pcDNA3-GLsp-nanoKAZ-AQQL, pcDNA3-GLsp-nanoKAZ-KVA and pcDNA3-GLsp-nanoKAZ-FLM. The gene sequence inserted was confirmed by sequencing using a DNA Sequencer (manufactured by ABI Inc.).

Example 7: Construction of Vectors for Secretory Expression of NanoKAZ Mutants in Animal Culture Cells without Using Secretory Signal Peptide Sequences The pcDNA3-GLsp-nanoKAZ-AQQL, pcDNA3-GLsp-nanoKAZ-KVA and pcDNA3-GLsp-nanoKAZ-FLM vectors obtained in EXAMPLE 6 were digested with the restriction enzymes of Asp718/XbaI in a conventional manner and the resultant DNA fragment was ligated to the Asp718/XbaI site of pcDNA3 vector (manufactured by Invitrogen Inc.) to construct pcDNA3-nanoKAZ-AQQL, pcDNA3-nanoKAZ-KVA and pcDNA3-nanoKAZ-FLM. The gene sequence inserted was confirmed by sequencing using a DNA Sequencer (manufactured by ABI Inc.).

Example 8: Transfection of Vectors to Animal Culture Cells and Preparation of Enzyme for Assay (1) Purification of Expression Plasmid The recombinant plasmids obtained in EXAMPLES 6 and 7 were purified from *E. coli* JM83 host strain using a plasmid purification kit (manufactured by QIAGEN) and dissolved in sterile water. The firefly luciferase vector (pGL4.13 [Luc2/sv40]: manufactured by Promega Corp.) was similarly prepared and used as an internal standard.

(2) Transfection and Preparation of Enzyme for Assay

Chinese hamster ovary cell line CHO-K1 was cultured in Ham's F-12 medium (manufactured by Wako Pure Chemical Industries, Ltd.) supplemented with 10% (v/v) fetal bovine serum (manufactured by Biowest Inc.). The CHO-K1 cells were seeded in a 6-well plate in $2 \times 10^5$ cells/well/2 mL medium (n=2) and cultured in an incubator at 37° C. in 5% (v/v) $CO_2$. After 24 hours, the purified recombinant plasmid was transfected to CHO-K1 cells using a FuGene HD transfection kit (manufactured by Promega Corp.) and the cells were provided for subsequent experiment. Specifically, 1 μg of the recombinant plasmid, 0.1 μg of the internal standard vector pGL4.13 [Luc2/sv40] and 3.3 μL of FuGene HD were added to 100 μL of the medium and allowed to stand at room temperature for 15 minutes. Subsequently, 100 μL of the DNA-FuGene complex solution was added to the cells in the 6-well plate. After incubation for 46 hours, the culture medium was collected.

Example 9: Assay for Luminescence Activity of NanoKAZ Mutants Expressed in the Medium of Animal Culture Cells The crude enzyme solution, 5 μl, obtained in EXAMPLE 8 was added to 100 μl of 30 mM Tris-HCl (pH 7.6)-10 mM EDTA (Wako Pure Chemical Industries, Ltd.) containing 1 μg of coelenterazine (manufactured by JNC Corp.), and the luminescence reaction was started. Luminescence activity was measured for 60 seconds using a luminometer (manufactured by Atto Inc.: AB2200); the maximum intensity of luminescence ($I_{max}$) and the integrated values for 60 seconds within parentheses in terms of relative intensity of luminescence are shown in TABLE 3.

Regarding firefly luciferase used as an internal standard to confirm the efficiency of transfection, 5 μL of the cell extract obtained in EXAMPLE 7 was added to 100 μL of a reagent for enzyme assay (Promega Corp.) to start a luminescence reaction. Luminescence activity was measured for 10 seconds in terms of the maximum intensity of luminescence ($I_{max}$), using a luminometer (manufactured by Atto Inc.: AB2200). It was confirmed by the results that the transfection efficiencies were almost the same. Therefore, the firefly luciferase was used as the internal standard to calculate the relative activity.

Example 10: Luminescence Activity and Substrate Specificity of NanoKAZ Mutants Secreted into the Culture Medium from Animal Culture Cells Using a Secretory Signal Peptide Sequences Luminescence activity of the nanoKAZ mutants secreted into the culture medium from animal cultured cells using the secretory signal peptide sequence was measured by the method described in EXAMPLE 9. The results are shown in TABLE 3. The results of TABLE 3 reveal that nanoKAZ-AQQL in the nanoKAZ mutants was secreted from the cells and showed approximately 20-fold higher luminescence activity than that of nanoKAZ when coelenterazine was used as the substrate. The nanoKAZ-AQQL mutant is secretable protein and can use coelenterazine as the most efficient substrate for the luminescence reaction.

TABLE 3

Luminescence activity and substrate specificity of nanoKAZ mutants secreted into the culture medium from animal culture cells using a secretory signal peptide sequence

| Luminescence substrate | Relative maximum intensity of luminescence $I_{max}$ (integrated values of relative intensity of luminescence for 1 min) | | | |
|---|---|---|---|---|
| | nanoKAZ | nanoKAZ-AQQL | nanoKAZ-KVA | nanoKAZ-FLM |
| Coelenterazine (CTZ) | 1.0 (1.0) | 20.0 (15.9) | 0.01 (0.004) | 0.1 (0.1) |
| bis-coelenterazine | 11.1 (11.1) | 1.8 (1.6) | 0.1 (0.06) | 3.4 (3.4) |
| h-coelenterazine | 16.4 (9.9) | 13.9 (3.3) | 0.1 (0.04) | 4.8 (3.4) |
| 6h-coelenterazine | 0.8 (0.7) | 2.3 (2.5) | 0.001 (0.001) | 0.1 (0.1) |
| f-coelenterazine | 21.6 (12.2) | 9.7 (3.8) | 0.2 (0.03) | 8.1 (4.8) |
| 6h-f-coelenterazine | 11.7 (11.8) | 1.1 (1.1) | 0.1 (0.08) | 5.5 (5.5) |
| Furimazine | 5.9 (6.2) | 0.7 (0.7) | 0.1 (0.05) | 1.5 (1.6) |

Example 11: Secretory Expression of NanoKAZ Mutants into the Culture Medium from Animal Culture Cells without Using a Secretory Signal Peptide Sequences Luminescence activity of the nanoKAZ mutants in culture medium, which were secreted from animal culture cells without using a secretory signal peptide sequence, was measured by the method described in EXAMPLE 9. The results are shown in TABLE 4. The results of TABLE 4 reveal that, among the nanoKAZ mutants carrying no signal peptide sequence for secretion, nanoKAZ-AQQL was secreted from the cells and showed approximately 18-fold higher luminescence activity than that of nanoKAZ, when coelenterazine was used as the substrate. This expression level of nanoKAZ-AQQL was similar to that of nanoKAZ-AQQL carrying the secretory signal peptide sequence described in TABLE 3, which shows about 20-fold activity of nanoKAZ. That is, nanoKAZ-AQQL is a secretable mutant in the absence of the secretory signal peptide sequence for secretion. As nanoKAZ secreted into the culture medium in the absence or presence of secretory signal peptide sequences is considered to have the similar basic structure in both proteins, their substrate specificities are likely to be the same. These results indicate that nanoKAZ-AQQL as a nanoKAZ mutant can be secreted from animal culture cells in the presence or absence of eukaryotic secretory signal peptide sequences and enables the most efficient use of coelenterazine as the substrate.

TABLE 4

Luminescence activity of nanoKAZ mutants expressed in culture medium of animal culture cells without using a secretory signal peptide sequence

| Luminescence substrate | Relative maximum intensity of luminescence $I_{max}$ (integrated values of relative intensity of luminescence for 1 min) | | | |
| --- | --- | --- | --- | --- |
| | nanoKAZ | nanoKAZ-AQQL | nanoKAZ-KVA | nanoKAZ-FLM |
| Coelenterazine (CTZ) | 1.0 (1.0) | 18.3 (15.2) | 0.003 (0.001) | 0.06 (0.1) |

[Sequence Listing Free Text]
[SEQ ID NO: 1] Nucleotide sequence of nanoKAZ.
[SEQ ID NO: 2] Amino acid sequence of nanoKAZ.
[SEQ ID NO: 3] Nucleotide sequence of nanoKAZ-AQQL.
[SEQ ID NO: 4] Amino acid sequence of nanoKAZ-AQQL.
[SEQ ID NO: 5] Nucleotide sequence of nanoKAZ-KVA.
[SEQ ID NO: 6] Amino acid sequence of nanoKAZ-KVA.
[SEQ ID NO: 7] Nucleotide sequence of nanoKAZ-FLM.
[SEQ ID NO: 8] Amino acid sequence of nanoKAZ-FLM.
[SEQ ID NO: 9] Nucleotide sequence of the primer used in EXAMPLES (nanoKAZ-1N/EcoRI).
[SEQ ID NO: 10] Nucleotide sequence of the primer used in EXAMPLES (nanoKAZ-3C/XbaI).
[SEQ ID NO: 11] Nucleotide sequence of the primer used in EXAMPLES (GLsp-1R/EcoRI)
[SEQ ID NO: 12] Nucleotide sequence of the primer used in EXAMPLES (T7).
[SEQ ID NO: 13] Nucleotide sequence of the primer used in EXAMPLES (nKAZ-2R/AQQL).
[SEQ ID NO: 14] Nucleotide sequence of the primer used in EXAMPLES (nKAZ-1F/AQQL).
[SEQ ID NO: 15] Nucleotide sequence of the primer used in EXAMPLES (BGH-R).
[SEQ ID NO: 16] Nucleotide sequence of the primer used in EXAMPLES (nKAZ-4R/KVA).
[SEQ ID NO: 17] Nucleotide sequence of the primer used in EXAMPLES (nKAZ-3F/KVA).
[SEQ ID NO: 18] Nucleotide sequence of the primer used in EXAMPLES (nKAZ-6R/FLM).
[SEQ ID NO: 19] Nucleotide sequence of the primer used in EXAMPLES (nKAZ-5F/FLM).

The invention claimed is:

1. A polynucleotide comprising a nucleotide sequence encoding a recombinant luciferase mutant of (a) or (b) below:
   (a) a recombinant luciferase mutant comprising the amino acid sequence of SEQ ID NO: 2 substituted at the amino acid positions consisting of:
   glutamic acid at position 4;
   arginine at position 11;
   leucine at position 18; and
   valine at position 27; or
   (b) a recombinant luciferase mutant comprising the amino acid sequence of SEQ ID NO: 2 substituted at the positions consisting of:
   glutamic acid at position 4;
   arginine at position 11;
   leucine at position 18;
   valine at position 27; and
   one or more amino acid(s) at position(s) other than positions 4, 11, 18, 27, 33, 43, 44, 54, 68, 72, 75, 90, 115, 124, 138, and 166 of the amino acid sequence of SEQ ID NO: 2, wherein the recombinant luciferase mutant has luciferase activity.

2. A recombinant vector comprising the polynucleotide of claim 1.

3. A transformant transformed with the recombinant vector of claim 2.

4. The polynucleotide of claim 1, wherein the recombinant luciferase mutant defined in (b) above is a recombinant luciferase mutant defined in (c) below:
   (c) a recombinant luciferase mutant comprising the amino acid sequence of SEQ ID NO: 2 substituted at the positions consisting of:

glutamic acid at position 4;
arginine at position 11;
leucine at position 18;
valine at position 27; and
1 to 16 amino acid(s) at position(s) other than positions 4, 11, 18, 27, 33, 43, 44, 54, 68, 72, 75, 90, 115, 124, 138, and 166 of the amino acid sequence of SEQ ID NO: 2, and wherein the recombinant luciferase mutant has luciferase activity.

5. The polynucleotide of claim 1, wherein glutamic acid at the amino position 4 is substituted with alanine, arginine at the amino acid position 11 is substituted with glutamine, leucine at the amino acid position 18 is substituted with glutamine, and valine at the amino acid position 27 is substituted with leucine.

6. The polynucleotide of claim 1, wherein the recombinant luciferase mutant defined in (a) or (b) above is a recombinant luciferase mutant defined in (d) or (e), respectively, below:

(d) a recombinant luciferase mutant comprising the amino acid sequence of SEQ ID NO: 4; or,
(e) a recombinant luciferase mutant comprising the amino acid sequence of SEQ ID NO: 4 in which one or more amino acid(s) at position(s) other than positions 4, 11, 18, 27, 33, 43, 44, 54, 68, 72, 75, 90, 115, 124, 138, and 166 of the amino acid sequence of SEQ ID NO: 4, and wherein the recombinant luciferase mutant has luciferase activity.

7. The polynucleotide of claim 6, wherein the recombinant luciferase mutant defined in (e) above is a recombinant luciferase mutant defined in (f) below:

(f) a recombinant luciferase mutant comprising the amino acid sequence of SEQ ID NO: 4 substituted in which 1 to 16 amino acid(s) at position(s) other than positions 4, 11, 18, 27, 33, 43, 44, 54, 68, 72, 75, 90, 115, 124, 138, and 166 of the amino acid sequence of SEQ ID NO: 4, and wherein the recombinant luciferase mutant has luciferase activity.

* * * * *

SEQUENCE LISTING

<160> NUMBER OF SEQ ID NOS: 19

<210> SEQ ID NO 1
<211> LENGTH: 510
<212> TYPE: DNA
<213> ORGANISM: Artificial Sequence
<220> FEATURE:
<223> OTHER INFORMATION: Synthetic Construct

```
<220> FEATURE:
<221> NAME/KEY: CDS
<222> LOCATION: (1)..(507)

<400> SEQUENCE: 1 ttc acc ctg gag gac ttc gtc ggc gac tgg aga cag acc gcc ggc tac      48
Phe Thr Leu Glu Asp Phe Val Gly Asp Trp Arg Gln Thr Ala Gly Tyr
1               5                   10                  15 aac ctg gac cag gtc ctg gag cag ggc ggc gtc agc agc ctg ttc cag      96
Asn Leu Asp Gln Val Leu Glu Gln Gly Gly Val Ser Ser Leu Phe Gln
            20                  25                  30 aac ctg ggc gtc agc gtc acc ccc atc cag aga atc gtc ctt agc ggc     144
Asn Leu Gly Val Ser Val Thr Pro Ile Gln Arg Ile Val Leu Ser Gly
        35                  40                  45 gag aac ggc ctg aag atc gac atc cac gtc atc atc ccc tac gag ggc     192
Glu Asn Gly Leu Lys Ile Asp Ile His Val Ile Ile Pro Tyr Glu Gly
    50                  55                  60 ctg agc ggc gac cag atg ggc cag atc gag aag atc ttc aag gtc gtc     240
Leu Ser Gly Asp Gln Met Gly Gln Ile Glu Lys Ile Phe Lys Val Val
65                  70                  75                  80 tac ccc gtc gac gac cac cac ttc aag gtc atc ctg cac tac ggc acc     288
Tyr Pro Val Asp Asp His His Phe Lys Val Ile Leu His Tyr Gly Thr
                85                  90                  95 ctg gtc atc gac ggc gtc acc ccc aac atg atc gac tac ttc ggt aga     336
Leu Val Ile Asp Gly Val Thr Pro Asn Met Ile Asp Tyr Phe Gly Arg
            100                 105                 110 ccc tac gag ggc atc gcc gtc ttc gac ggc aag aag atc acc gtc acc     384
Pro Tyr Glu Gly Ile Ala Val Phe Asp Gly Lys Lys Ile Thr Val Thr
        115                 120                 125 ggc acc ctg tgg aac ggc aac aag atc atc gac gag aga ctg atc aac     432
Gly Thr Leu Trp Asn Gly Asn Lys Ile Ile Asp Glu Arg Leu Ile Asn
    130                 135                 140 ccc gac ggc agc ctg ctg ttc aga gtc acc atc aac ggc gtc acc ggc     480
Pro Asp Gly Ser Leu Leu Phe Arg Val Thr Ile Asn Gly Val Thr Gly
145                 150                 155                 160 tgg aga ctg tgc gag aga atc ctg gcc taa                             510
Trp Arg Leu Cys Glu Arg Ile Leu Ala
                165

<210> SEQ ID NO 2
<211> LENGTH: 169
<212> TYPE: PRT
<213> ORGANISM: Artificial Sequence
<220> FEATURE:
<223> OTHER INFORMATION: Synthetic Construct

<400> SEQUENCE: 2

Phe Thr Leu Glu Asp Phe Val Gly Asp Trp Arg Gln Thr Ala Gly Tyr
1               5                   10                  15

Asn Leu Asp Gln Val Leu Glu Gln Gly Gly Val Ser Ser Leu Phe Gln
            20                  25                  30

Asn Leu Gly Val Ser Val Thr Pro Ile Gln Arg Ile Val Leu Ser Gly
        35                  40                  45

Glu Asn Gly Leu Lys Ile Asp Ile His Val Ile Ile Pro Tyr Glu Gly
    50                  55                  60

Leu Ser Gly Asp Gln Met Gly Gln Ile Glu Lys Ile Phe Lys Val Val
65                  70                  75                  80

Tyr Pro Val Asp Asp His His Phe Lys Val Ile Leu His Tyr Gly Thr
                85                  90                  95
```

```
Leu Val Ile Asp Gly Val Thr Pro Asn Met Ile Asp Tyr Phe Gly Arg
            100                 105                 110

Pro Tyr Glu Gly Ile Ala Val Phe Asp Gly Lys Lys Ile Thr Val Thr
        115                 120                 125

Gly Thr Leu Trp Asn Gly Asn Lys Ile Ile Asp Glu Arg Leu Ile Asn
    130                 135                 140

Pro Asp Gly Ser Leu Leu Phe Arg Val Thr Ile Asn Gly Val Thr Gly
145                 150                 155                 160

Trp Arg Leu Cys Glu Arg Ile Leu Ala
                165
```

```
<210> SEQ ID NO 3
<211> LENGTH: 510
<212> TYPE: DNA
<213> ORGANISM: Artificial
<220> FEATURE:
<223> OTHER INFORMATION: Synthetic Construct
<220> FEATURE:
<221> NAME/KEY: CDS
<222> LOCATION: (1)..(507)

<400> SEQUENCE: 3
```

```
ttc acc ctg gca gac ttc gtc ggc gac tgg caa cag acc gcc ggc tac    48
Phe Thr Leu Ala Asp Phe Val Gly Asp Trp Gln Gln Thr Ala Gly Tyr
1               5                  10                  15 aac caa gac cag gtc ctg gag cag ggc ggc ttg agc agc ctg ttc cag    96
Asn Gln Asp Gln Val Leu Glu Gln Gly Gly Leu Ser Ser Leu Phe Gln
            20                  25                  30 aac ctg ggc gtc agc gtc acc ccc atc cag aga atc gtc ctt agc ggc   144
Asn Leu Gly Val Ser Val Thr Pro Ile Gln Arg Ile Val Leu Ser Gly
        35                  40                  45 gag aac ggc ctg aag atc gac atc cac gtc atc atc ccc tac gag ggc   192
Glu Asn Gly Leu Lys Ile Asp Ile His Val Ile Ile Pro Tyr Glu Gly
    50                  55                  60 ctg agc ggc gac cag atg ggc cag atc gag aag atc ttc aag gtc gtc   240
Leu Ser Gly Asp Gln Met Gly Gln Ile Glu Lys Ile Phe Lys Val Val
65                  70                  75                  80 tac ccc gtc gac gac cac cac ttc aag gtc atc ctg cac tac ggc acc   288
Tyr Pro Val Asp Asp His His Phe Lys Val Ile Leu His Tyr Gly Thr
                85                  90                  95 ctg gtc atc gac ggc gtc acc ccc aac atg atc gac tac ttc ggt aga   336
Leu Val Ile Asp Gly Val Thr Pro Asn Met Ile Asp Tyr Phe Gly Arg
            100                 105                 110 ccc tac gag ggc atc gcc gtc ttc gac ggc aag aag atc acc gtc acc   384
Pro Tyr Glu Gly Ile Ala Val Phe Asp Gly Lys Lys Ile Thr Val Thr
        115                 120                 125 ggc acc ctg tgg aac ggc aac aag atc atc gac gag aga ctg atc aac   432
Gly Thr Leu Trp Asn Gly Asn Lys Ile Ile Asp Glu Arg Leu Ile Asn
    130                 135                 140 ccc gac ggc agc ctg ctg ttc aga gtc acc atc aac ggc gtc acc ggc   480
Pro Asp Gly Ser Leu Leu Phe Arg Val Thr Ile Asn Gly Val Thr Gly
145                 150                 155                 160 tgg aga ctg tgc gag aga atc ctg gcc taa                           510
Trp Arg Leu Cys Glu Arg Ile Leu Ala
                165
```

```
<210> SEQ ID NO 4
<211> LENGTH: 169
<212> TYPE: PRT
<213> ORGANISM: Artificial
<220> FEATURE:
<223> OTHER INFORMATION: Synthetic Construct
```

<400> SEQUENCE: 4

Phe Thr Leu Ala Asp Phe Val Gly Asp Trp Gln Gln Thr Ala Gly Tyr
1               5                   10                  15

Asn Gln Asp Gln Val Leu Glu Gln Gly Gly Leu Ser Ser Leu Phe Gln
            20                  25                  30

Asn Leu Gly Val Ser Val Thr Pro Ile Gln Arg Ile Val Leu Ser Gly
        35                  40                  45

Glu Asn Gly Leu Lys Ile Asp Ile His Val Ile Ile Pro Tyr Glu Gly
    50                  55                  60

Leu Ser Gly Asp Gln Met Gly Gln Ile Glu Lys Ile Phe Lys Val Val
65                  70                  75                  80

Tyr Pro Val Asp Asp His His Phe Lys Val Ile Leu His Tyr Gly Thr
                85                  90                  95

Leu Val Ile Asp Gly Val Thr Pro Asn Met Ile Asp Tyr Phe Gly Arg
            100                 105                 110

Pro Tyr Glu Gly Ile Ala Val Phe Asp Gly Lys Lys Ile Thr Val Thr
        115                 120                 125

Gly Thr Leu Trp Asn Gly Asn Lys Ile Ile Asp Glu Arg Leu Ile Asn
    130                 135                 140

Pro Asp Gly Ser Leu Leu Phe Arg Val Thr Ile Asn Gly Val Thr Gly
145                 150                 155                 160

Trp Arg Leu Cys Glu Arg Ile Leu Ala
                165

<210> SEQ ID NO 5
<211> LENGTH: 510
<212> TYPE: DNA
<213> ORGANISM: Artificial Sequence
<220> FEATURE:
<223> OTHER INFORMATION: Synthetic Construct
<220> FEATURE:
<221> NAME/KEY: CDS
<222> LOCATION: (1)..(507)

<400> SEQUENCE: 5 ttc acc ctg gag gac ttc gtc ggc gac tgg aga cag acc gcc ggc tac      48
Phe Thr Leu Glu Asp Phe Val Gly Asp Trp Arg Gln Thr Ala Gly Tyr
1               5                   10                  15 aac ctg gac cag gtc ctg gag cag ggc ggc gtc agc agc ctg ttc cag      96
Asn Leu Asp Gln Val Leu Glu Gln Gly Gly Val Ser Ser Leu Phe Gln
            20                  25                  30 aac ctg ggc gtc agc gtc acc ccc atc cag aaa gtt gtc ctt agc ggc      144
Asn Leu Gly Val Ser Val Thr Pro Ile Gln Lys Val Val Leu Ser Gly
        35                  40                  45 gag aac ggc ctg aag gct gac atc cac gtc atc atc ccc tac gag ggc      192
Glu Asn Gly Leu Lys Ala Asp Ile His Val Ile Ile Pro Tyr Glu Gly
    50                  55                  60 ctg agc ggc gac cag atg ggc cag atc gag aag atc ttc aag gtc gtc      240
Leu Ser Gly Asp Gln Met Gly Gln Ile Glu Lys Ile Phe Lys Val Val
65                  70                  75                  80 tac ccc gtc gac gac cac cac ttc aag gtc atc ctg cac tac ggc acc      288
Tyr Pro Val Asp Asp His His Phe Lys Val Ile Leu His Tyr Gly Thr
                85                  90                  95 ctg gtc atc gac ggc gtc acc ccc aac atg atc gac tac ttc ggt aga      336
Leu Val Ile Asp Gly Val Thr Pro Asn Met Ile Asp Tyr Phe Gly Arg
            100                 105                 110 ccc tac gag ggc atc gcc gtc ttc gac ggc aag aag atc acc gtc acc      384
Pro Tyr Glu Gly Ile Ala Val Phe Asp Gly Lys Lys Ile Thr Val Thr
        115                 120                 125

```
ggc acc ctg tgg aac ggc aac aag atc atc gac gag aga ctg atc aac      432
Gly Thr Leu Trp Asn Gly Asn Lys Ile Ile Asp Glu Arg Leu Ile Asn
        130                 135                 140 ccc gac ggc agc ctg ctg ttc aga gtc acc atc aac ggc gtc acc ggc      480
Pro Asp Gly Ser Leu Leu Phe Arg Val Thr Ile Asn Gly Val Thr Gly
145                 150                 155                 160 tgg aga ctg tgc gag aga atc ctg gcc taa                              510
Trp Arg Leu Cys Glu Arg Ile Leu Ala
                165
```

<210> SEQ ID NO 6
<211> LENGTH: 169
<212> TYPE: PRT
<213> ORGANISM: Artificial Sequence
<220> FEATURE:
<223> OTHER INFORMATION: Synthetic Construct

<400> SEQUENCE: 6

```
Phe Thr Leu Glu Asp Phe Val Gly Asp Trp Arg Gln Thr Ala Gly Tyr
1               5                   10                  15

Asn Leu Asp Gln Val Leu Glu Gln Gly Gly Val Ser Ser Leu Phe Gln
            20                  25                  30

Asn Leu Gly Val Ser Val Thr Pro Ile Gln Lys Val Val Leu Ser Gly
        35                  40                  45

Glu Asn Gly Leu Lys Ala Asp Ile His Val Ile Pro Tyr Glu Gly Leu
    50                  55                  60

Leu Ser Gly Asp Gln Met Gly Gln Ile Glu Lys Ile Phe Lys Val Val
65                  70                  75                  80

Tyr Pro Val Asp Asp His His Phe Lys Val Ile Leu His Tyr Gly Thr
                85                  90                  95

Leu Val Ile Asp Gly Val Thr Pro Asn Met Ile Asp Tyr Phe Gly Arg
            100                 105                 110

Pro Tyr Glu Gly Ile Ala Val Phe Asp Gly Lys Lys Ile Thr Val Thr
        115                 120                 125

Gly Thr Leu Trp Asn Gly Asn Lys Ile Ile Asp Glu Arg Leu Ile Asn
    130                 135                 140

Pro Asp Gly Ser Leu Leu Phe Arg Val Thr Ile Asn Gly Val Thr Gly
145                 150                 155                 160

Trp Arg Leu Cys Glu Arg Ile Leu Ala
                165
```

<210> SEQ ID NO 7
<211> LENGTH: 510
<212> TYPE: DNA
<213> ORGANISM: Artificial Sequence
<220> FEATURE:
<223> OTHER INFORMATION: Synthetic Construct
<220> FEATURE:
<221> NAME/KEY: CDS
<222> LOCATION: (1)..(507)

<400> SEQUENCE: 7

```
ttc acc ctg gag gac ttc gtc ggc gac tgg aga cag acc gcc ggc tac       48
Phe Thr Leu Glu Asp Phe Val Gly Asp Trp Arg Gln Thr Ala Gly Tyr
1               5                   10                  15 aac ctg gac cag gtc ctg gag cag ggc ggc gtc agc agc ctg ttc cag       96
Asn Leu Asp Gln Val Leu Glu Gln Gly Gly Val Ser Ser Leu Phe Gln
            20                  25                  30
```

| | | |
|---|---|---|
| aac ctg ggc gtc agc gtc acc ccc atc cag aga atc gtc ctt agc ggc<br>Asn Leu Gly Val Ser Val Thr Pro Ile Gln Arg Ile Val Leu Ser Gly<br>35 40 45 | | 144 |
| gag aac ggc ctg aag atc gac atc cac gtc atc atc ccc tac gag ggc<br>Glu Asn Gly Leu Lys Ile Asp Ile His Val Ile Ile Pro Tyr Glu Gly<br>50 55 60 | | 192 |
| ctg agc ggc ttt cag atg ggc cta atc gag atg atc ttc aag gtc gtc<br>Leu Ser Gly Phe Gln Met Gly Leu Ile Glu Met Ile Phe Lys Val Val<br>65 70 75 80 | | 240 |
| tac ccc gtc gac gac cac cac ttc aag gtc atc ctg cac tac ggc acc<br>Tyr Pro Val Asp Asp His His Phe Lys Val Ile Leu His Tyr Gly Thr<br>85 90 95 | | 288 |
| ctg gtc atc gac ggc gtc acc ccc aac atg atc gac tac ttc ggt aga<br>Leu Val Ile Asp Gly Val Thr Pro Asn Met Ile Asp Tyr Phe Gly Arg<br>100 105 110 | | 336 |
| ccc tac gag ggc atc gcc gtc ttc gac ggc aag aag atc acc gtc acc<br>Pro Tyr Glu Gly Ile Ala Val Phe Asp Gly Lys Lys Ile Thr Val Thr<br>115 120 125 | | 384 |
| ggc acc ctg tgg aac ggc aac aag atc atc gac gag aga ctg atc aac<br>Gly Thr Leu Trp Asn Gly Asn Lys Ile Ile Asp Glu Arg Leu Ile Asn<br>130 135 140 | | 432 |
| ccc gac ggc agc ctg ctg ttc aga gtc acc atc aac ggc gtc acc ggc<br>Pro Asp Gly Ser Leu Leu Phe Arg Val Thr Ile Asn Gly Val Thr Gly<br>145 150 155 160 | | 480 |
| tgg aga ctg tgc gag aga atc ctg gcc taa<br>Trp Arg Leu Cys Glu Arg Ile Leu Ala<br>165 | | 510 |

<210> SEQ ID NO 8
<211> LENGTH: 169
<212> TYPE: PRT
<213> ORGANISM: Artificial Sequence
<220> FEATURE:
<223> OTHER INFORMATION: Synthetic Construct

<400> SEQUENCE: 8

Phe Thr Leu Glu Asp Phe Val Gly Asp Trp Arg Gln Thr Ala Gly Tyr
1               5                   10                  15

Asn Leu Asp Gln Val Leu Glu Gln Gly Gly Val Ser Ser Leu Phe Gln
            20                  25                  30

Asn Leu Gly Val Ser Val Thr Pro Ile Gln Arg Ile Val Leu Ser Gly
        35                  40                  45

Glu Asn Gly Leu Lys Ile Asp Ile His Val Ile Ile Pro Tyr Glu Gly
    50                  55                  60

Leu Ser Gly Phe Gln Met Gly Leu Ile Glu Met Ile Phe Lys Val Val
65                  70                  75                  80

Tyr Pro Val Asp Asp His His Phe Lys Val Ile Leu His Tyr Gly Thr
                85                  90                  95

Leu Val Ile Asp Gly Val Thr Pro Asn Met Ile Asp Tyr Phe Gly Arg
            100                 105                 110

Pro Tyr Glu Gly Ile Ala Val Phe Asp Gly Lys Lys Ile Thr Val Thr
        115                 120                 125

Gly Thr Leu Trp Asn Gly Asn Lys Ile Ile Asp Glu Arg Leu Ile Asn
    130                 135                 140

Pro Asp Gly Ser Leu Leu Phe Arg Val Thr Ile Asn Gly Val Thr Gly
145                 150                 155                 160

Trp Arg Leu Cys Glu Arg Ile Leu Ala
                165

```
<210> SEQ ID NO 9
<211> LENGTH: 33
<212> TYPE: DNA
<213> ORGANISM: Artificial Sequence
<220> FEATURE:
<223> OTHER INFORMATION: Synthetic polynucleotide

<400> SEQUENCE: 9
gcggaattct tcaccctgga ggacttcgtc ggc                                    33

<210> SEQ ID NO 10
<211> LENGTH: 36
<212> TYPE: DNA
<213> ORGANISM: Artificial Sequence
<220> FEATURE:
<223> OTHER INFORMATION: Synthetic polynucleotide

<400> SEQUENCE: 10
gcctctagat taggccagga ttctctcgca cagtct                                 36

<210> SEQ ID NO 11
<211> LENGTH: 30
<212> TYPE: DNA
<213> ORGANISM: Artificial Sequence
<220> FEATURE:
<223> OTHER INFORMATION: Synthetic polynucleotide

<400> SEQUENCE: 11
ggcgaattcg gtgggcttgg cctcggccac                                        30

<210> SEQ ID NO 12
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 12
taatacgact cactataggg                                                   20

<210> SEQ ID NO 13
<211> LENGTH: 93
<212> TYPE: DNA
<213> ORGANISM: Artificial Sequence
<220> FEATURE:
<223> OTHER INFORMATION: Synthetic polynucleotide

<400> SEQUENCE: 13
caggctgctc aagccgccct gctccaggac ctggtcttgg ttgtagccgg cggtctgttg       60
ccagtcgccg acgaagtctg ccagggtgaa gac                                    93

<210> SEQ ID NO 14
<211> LENGTH: 93
<212> TYPE: DNA
<213> ORGANISM: Artificial Sequence
<220> FEATURE:
<223> OTHER INFORMATION: Synthetic polynucleotide

<400> SEQUENCE: 14
ttcaccctgg cagacttcgt cggcgactgg caacagaccg ccggctacaa ccaagaccag       60
gtcctggagc agggcggctt gagcagcctg ttc                                    93
```

```
<210> SEQ ID NO 15
<211> LENGTH: 18
<212> TYPE: DNA
<213> ORGANISM: Artificial Sequence
<220> FEATURE:
<223> OTHER INFORMATION: Synthetic polynucleotide

<400> SEQUENCE: 15
tagaaggcac agtcgagg                                                    18

<210> SEQ ID NO 16
<211> LENGTH: 57
<212> TYPE: DNA
<213> ORGANISM: Artificial Sequence
<220> FEATURE:
<223> OTHER INFORMATION: Synthetic polynucleotide

<400> SEQUENCE: 16
gtggatgtca gccttcaggc cgttctcgcc gctaaggaca actttctgga tgggggt         57

<210> SEQ ID NO 17
<211> LENGTH: 57
<212> TYPE: DNA
<213> ORGANISM: Artificial Sequence
<220> FEATURE:
<223> OTHER INFORMATION: Synthetic polynucleotide

<400> SEQUENCE: 17
cccatccaga aagttgtcct tagcggcgag aacggcctga aggctgacat ccacgtc         57

<210> SEQ ID NO 18
<211> LENGTH: 45
<212> TYPE: DNA
<213> ORGANISM: Artificial Sequence
<220> FEATURE:
<223> OTHER INFORMATION: Synthetic polynucleotide

<400> SEQUENCE: 18
cttgaagatc atctcgatta ggcccatctg aaagccgctc aggcc                      45

<210> SEQ ID NO 19
<211> LENGTH: 45
<212> TYPE: DNA
<213> ORGANISM: Artificial Sequence
<220> FEATURE:
<223> OTHER INFORMATION: Synthetic polynucleotide

<400> SEQUENCE: 19
ctgagcggct ttcagatggg cctaatcgag atgatcttca aggtc                      45
```